(12) United States Patent
Stransky

(10) Patent No.: US 10,370,723 B2
(45) Date of Patent: Aug. 6, 2019

(54) TERT FUSIONS

(71) Applicant: BLUEPRINT MEDICINES CORPORATION, Cambridge, MA (US)

(72) Inventor: Nicolas Stransky, Charlestown, MA (US)

(73) Assignee: Blueprint Medicines Corporation, Cambridge, MA (US)

( * ) Notice: Subject to any disclaimer, the term of this patent is extended or adjusted under 35 U.S.C. 154(b) by 0 days.

(21) Appl. No.: 15/326,350

(22) PCT Filed: Jul. 15, 2015

(86) PCT No.: PCT/US2015/040557
§ 371 (c)(1),
(2) Date: Jan. 13, 2017

(87) PCT Pub. No.: WO2016/011144
PCT Pub. Date: Jan. 21, 2016

(65) Prior Publication Data
US 2017/0198356 A1    Jul. 13, 2017

Related U.S. Application Data

(60) Provisional application No. 62/025,872, filed on Jul. 17, 2014.

(51) Int. Cl.
*C12Q 1/68* (2018.01)
*C07H 21/04* (2006.01)
*C12Q 1/6886* (2018.01)
*C07K 16/40* (2006.01)
*G01N 33/574* (2006.01)

(52) U.S. Cl.
CPC ............ *C12Q 1/6886* (2013.01); *C07K 16/40* (2013.01); *C12Y 207/07049* (2013.01); *C12Y 207/11001* (2013.01); *G01N 33/5748* (2013.01); *G01N 33/57407* (2013.01); *C07K 2317/34* (2013.01); *C12Q 2600/156* (2013.01); *C12Q 2600/158* (2013.01); *G01N 2333/912* (2013.01); *G01N 2333/9128* (2013.01)

(58) Field of Classification Search
None
See application file for complete search history.

(56) References Cited

FOREIGN PATENT DOCUMENTS

| WO | WO 2004/099385 A2 | 11/2004 |
|----|---|---|
| WO | WO 2008/043760 A1 | 4/2008 |
| WO | WO 2013/173912 A1 | 11/2013 |

OTHER PUBLICATIONS

Delespaul et al. (American Association for Cancer Research, "Recurrent TRIO fusion in non-translocation-related sarcomas", Aug. 15, 2016) (Year: 2016).*

(Continued)

*Primary Examiner* — Jeanine A Goldberg
(74) *Attorney, Agent, or Firm* — Finnegan, Henderson, Farabow, Garrett & Dunner, LLP

(57) ABSTRACT

The invention provides TERT gene fusions, TERT fusion proteins, and fragments of those genes and polypeptides. The invention further provides methods of diagnosing diseases or disorders associated with TERT fusions, such as conditions mediated by aberrant TERT expression or activity, or overexpression of TERT.

5 Claims, 5 Drawing Sheets
Specification includes a Sequence Listing.

(56) References Cited

OTHER PUBLICATIONS

International Patent Application No. PCT/US2015/040557, filed Jul. 15, 2015, by Blueprint Medicines Corp.: International Search Report and Written Opinion, dated Nov. 9, 2015.
Adamowicz, M. et al. (2006) "Frequent Amplifications and Abundant Expression of *TRIO, NKD2,* and *IRX2* in Soft Tissue Sarcomas" *Genes, Chromosomes & Cancer*, 45:829-838.
Breault, D.T. et al. (2008) "Generation of *mTERT*-GFP mice as a model to identify and study tissue progenitor cells" *PNAS*, 105(30):10420-10425.
GenBank Accession No. NM_007118, "*Homo sapiens* trio Rho guanine nucleotide exchange factor (TRIO), transcript variant 1, mRNA" PRI Jun. 10, 2017, 10 pages.
GenBank Accession No. NM_198253, "*Homo sapiens* telomerase reverse transcriptase (TERT), transcript variant 1, mRNA" PRI Jun. 11, 2017, 7 pages.
Huang, F.W. et al. (2013) "Highly recurrent *TERT* promoter mutations in human melanoma" *Science*, 339(6122):957-959. HHS Author Manuscript; available in PMC May 7, 2015, 6 pages.
Karlsson, J. et al. (2015) "Activation of human telomerase reverse transcriptase through gene fusion in clear cell sarcoma of the kidney" *Cancer Letters*, 357:498-501.
Soda, M. et al. (2007) "Identification of the transforming *EML4-ALK* fusion gene in non-small-cell lung cancer" *Nature*, 448:561-566.
Stransky, N. et al. (2014) "The landscape of kinase fusions in cancer" *Nat Commun,* 5:4846, DOI: 10.1038/ncomms5846, 10 pages.
Zhang, A. et al. (2000) "Frequent Amplification of the Telomerase Reverse Transcriptase Gene in Human Tumors" *Cancer Res,* 60:6230-6235.

\* cited by examiner

FIG. 1A

```
ATGAGCGGCA GCAGCGGCGG AGCCGCCGCC CCCGCCGCGT CCTCCGGCCC CGCCGCGGCG   60
GCCAGCGCGG CTGGCTCGGG CTGCGGGGGC GGTGCCGGCG AGGGGGCAGA GGAGGCGGCC  120
AAGGACCTGG CCGACATCGC GGCCTTCTTC CGATCCGGGT TTCGAAAAAA CGATGAAATG  180
AAAGCTATGG ATGTTTTACC AATTTTGAAG GAAAAAGTTG CATACCTTTC AGGTGGGAGA  240
GATAAACGTG GAGGTCCCAT TTTAACGTTT CCGGCCCGCA GCAATCATGA CAGAATACGA  300
CAGGAGGATC TCAGGAGACT CATTTCCTAT CTAGCCTGTA TTCCCAGCGA GGAGGTCTGC  360
AAGCGTGGCT TCACGGTGAT CGTGGACATG CGTGGGTCCA AGTGGGACTC CATCAAGCCC  420
CTTCTGAAGA TCCTGCAGGA GTCCTTCCCC TGCTGCATCC ATGTGGCCCT GATCATCAAG  480
CCAGACAACT TCTGGCAGAA ACAGAGGACT AATTTTGGCA GTTCTAAATT TGAATTTGAG  540
ACAAATATGG TCTCTTTAGA AGGCCTTACC AAAGTAGTTG ATCCTTCTCA GCTAACTCCT  600
GAGTTTGATG GCTGCCTGGA ATACAACCAC GAAGAATGGA TTGAAATCAG AGTTGCTTTT  660
GAAGACTACA TTAGCAATGC CACCCACATG CTGTCTCGGC TGGAGGAACT TCAGGACATC  720
CTAGCTAAGA AGGAGCTGCC TCAGGATTTA GAGGGGGCTC GGAATATGAT CGAGGAACAT  780
TCTCAGCTGA AGAAGAAGGT GATTAAGGCC CCCATCGAGG ACCTGGATTT GGAGGGACAG  840
AAGCTGCTTC AGAGGATACA GAGCAGTGAA AGCTTTCCCA AAAAGAACTC AGGCTCAGGC  900
AATGCGGACC TGCAGAACCT CTTGCCCAAG GTGTCCACCA TGCTGGACCG GCTGCACTCG  960
ACACGGCAGC ATCTGCACCA GATGTGGCAT GTGAGGAAGC TGAAGCTGGA CCAGTGCTTC 1020
CAGCTGAGGC TGTTTGAACA GGATGCTGAG AAGATGTTTG ACTGGATCAC ACACAACAAA 1080
GGCCTGTTTC TAAACAGCTA CACAGAGATT GGGACCAGCC ACCCTCATGC CATGGAGCTT 1140
CAGACGCAGC ACAATCACTT TGCCATGAAC TGTATGAACG TGTATGTAAA TATAAACCGC 1200
ATCATGTCGG TGGCCAATCG TCTGGTGGAG TCTGGCCACT ATGCCTCGCA GCAGATCAGG 1260
CAGATCGCGA GTCAGCTGGA GCAGGAGTGG AAGGCGTTTG CGGCAGCCCT GGATGAGCGG 1320
AGCACCTTGC TGGACATGTC CTCCATTTTC CACCAGAAGG CCGAAAAGTA TATGAGCAAC 1380
GTGGATTCAT GGTGTAAAGC TTGCGGTGAG GTAGACCTTC CCTCAGAGCT GCAGGACCTA 1440
GAAGATGCCA TTCATCACCA CCAGGGAATA TATGAACATA TCACTCTTGC TTATTCTGAG 1500
GTCAGCCAAG ATGGGAAGTC GCTCCTTGAC AAGCTCCAGC GGCCCTTGAC TCCCGGCAGC 1560
TCCGATTCCC TGACAGCCTC TGCCAACTAC TCCAAGGCCG TGCACCATGT CCTGGATGTC 1620
ATCCACGAGG TGCTGCACCA CCAGCGGCAG CTGGAGAACA TCTGGCAACA CCGCAAGGTC 1680
CGGCTGCATC AGAGGCTGCA GCTGTGTGTT TTCCAGCAGG ACGTTCAGCA GGTGCTAGAC 1740
TGGATCGAGA ACCACGGAGA AGCATTTCTG AGCAAACATA CAGGTGTGGG GAAATCTCTT 1800
CATCGGGCCA GAGCATTGCA GAAACGTCAT GAAGATTTTG AAGAAGTGGC ACAGAACACA 1860
TACACCAATG CGGATAAATT ACTGGAAGCA GCAGAACAGC TGGCTCAGAC TGGGGAATGT 1920
GACCCCGAAG AGATTTATCA GGCTGCCCAT CAGCTGGAAG ACCGGATTCA AGATTTCGTT 1980
CGGCGTGTTG AGCAGCGAAA GATCCTACTG GACATGTCAG TGTCCTTTCA CACCCATGTG 2040
AAAGAGCTGT GGACGTGGCT GGAGGAGCTG CAGAAGGAGC TGCTGGACGA CGTGTATGCC 2100
GAGTCGGTGG AGGCCGTGCA GGACCTCATC AAGCGCTTTG CCAGCAGCA GCAGACCACC 2160
CTGCAGGTGA CTGTCAACGT GATCAAGGAA GGGGAGGACC TCATCCAGCA GCTCAGGGAC 2220
TCTGCCATCT CCAGTAACAA GACCCCCCAC AACAGCTCCA TCAACCACAT TGAGACGGTG 2280
CTGCAGCAGC TGGACGAGGC GCAGTCGCAG ATGGAGGAGC TCTTCCAGGA GCGCAAGATC 2340
AAGCTGGAGC TCTTCCTGCA GCTGCGCATC TTCGAGAGGG ACGCCATCGA CATTATCTCA 2400
GACCTCGAGT CTTGGAATGA TGAGCTTTCT CAGCAAATGA ATGACTTCGA CACAGAAGAT 2460
CTCACGATTG CAGAGCAGCG CCTCCAGCAC CATGCAGACA AAGCCTTGAC CATGAACAAC 2520
TTGACTTTTG ACGTCATCCA CCAAGGGCAA GATCTTCTGC AGTATGTCAA TGAGGTCCAG 2580
GCCTCTGGTG TGGAGCTGCT GTGTGATAGA GATGTAGACA TGGCAACTCG GGTCCAGGAC 2640
CTGCTGGAGT TTCTTCATGA AAAACAGCAG GAATTGGATT TAGCCGCAGA GCAGCATCGG 2700
AAACACCTGG AGCAGTGCGT GCAGCTGCGC CACCTGCAGG CAGAAGTGAA ACAGGTGCTG 2760
GGTTGGATCC GCAACGGAGA GTCCATGTTA AATGCCGGAC TTATCACAGC CAGCTCGTTA 2820
CAAGAGGCAG AGCAGCTCCA GCGAGAGCAC GAGCAGTTCC AGCATGCCAT TGAGAAAACA 2880
CATCAGAGCG CGCTGCAGGT GCAGCAGAAG GCAGAAGCCA TGCTACAGGC CAACCACTAC 2940
GACATGGACA TGATCCGGGA CTGCGCCGAG AAGGTGGCGT CTCACTGGCA ACAGCTCATG 3000
CTCAAGATGG AAGATCGCCT CAAGCTCGTC AACGCCTCTG TCGCTTTCTA CAAAACCTCA 3060
```

FIG. 1B

```
GAGCAGGTCT GCAGCGTCCT CGAGAGCCTG GAACAGGAGT ACAAGAGAGA AGAAGACTGG 3120
TGTGGCGGGG CGGATAAGCT GGGCCCAAAC TCTGAGACGG ACCACGTGAC GCCCATGATC 3180
AGCAAGCACC TGGAGCAGAA GGAGGCATTC CTGAAGGCTT GCACCCTTGC TCGGAGGAAT 3240
GCAGACGTCT TCCTGAAATA CCTGCACAGG AACAGCGTGA ACATGCCAGG AATGGTGACG 3300
CACATCAAAG CTCCTGAACA GCAAGTGAAA AATATCTTGA ATGAACTCTT CCAACGGGAG 3360
AACAGGGTAT TGCATTACTG GACCATGAGG AAGAGACGGC TGGACCAGTG TCAGCAGTAC 3420
GTGGTCTTTG AGAGGAGTGC CAAGCAGGCT TTGGAATGGA TCCATGACAA TGGCGAGTTC 3480
TACCTTTCCA CACACACCTC CACGGGCTCC AGTATACAGC ACACCCAGGA GCTCCTGAAA 3540
GAGCACGAGG AGTTCCAGAT AACTGCAAAG CAAACCAAAG AGAGAGTGAA GCTATTGATA 3600
CAGCTGGCTG ATGGCTTTTG TGAAAAAGGG CATGCCCATG CGGCAGAGAT AAAAAAATGT 3660
GTTACTGCTG TGGATAAGAG GTACAGAGAT TTCTCTCTGC GGATGGAGAA GTACAGGACC 3720
TCTTTGGAAA AAGCCCTGGG GATTTCTTCA GATTCCAACA AATCGAGTAA AAGTCTCCAG 3780
CTAGATATCA TTCCAGCCAG TATCCCTGGC TCAGAGGTGA AACTTCGAGA TGCTGCTCAT 3840
GAACTTAATG AAGAGAAGCG GAAATCTGCC CGCAGGAAAG AGTTCATAAT GGCTGAGCTC 3900
ATTCAAACTG AAAAGGCTTA TGTAAGAGAC CTCCGGGAAT GTATGGATAC GTACCTGTGG 3960
GAAATGACCA GTGGCGTGGA AGAGATTCCA CCTGGCATTG TAAACAAAGA ACTCATCATC 4020
TTCGGAAACA TGCAAGAAAT CTACGAATTT CATAATAACA TATTCCTAAA GGAGCTGGAA 4080
AAATATGAAC AGTTGCCAGA GGATGTTGGA CATTGTTTTG TTACTTGGGC AGACAAGTTT 4140
CAGATGTATG TCACATATTG CAAAAATAAG CCTGATTCTA CTCAGCTGAT ATTGGAACAT 4200
GCAGGGTCCT ATTTTGACGA GATACAGCAG CGACATGGAT TAGCCAATTC CATTTCTTCC 4260
TACCTTATTA AACCAGTTCA GCGAATAACG AAGTATCAGC TCCTTTTAAA AGAGCTGCTG 4320
ACGTGCTGTG AGGAAGGAAA GGGAGAGATT AAAGATGGCC TGGAGGTGAT GCTCAGCGTG 4380
CCGAAGCGAG CCAATGATGC CATGCACCTC AGCATGCTGG AAGGGTTTGA TGAAAACATT 4440
GAGTCTCAGG GAGAACTCAT CCTACAGGAA TCCTTCCAAG TGTGGGACCC AAAAACCTTA 4500
ATTCGAAAGG GTCGAGAACG GCATCTCTTC CTTTTTGAAA TGTCCTTAGT ATTTAGTAAA 4560
GAAGTGAAAG ATTCCAGTGG GAGAAGCAAG TACCTTTATA AAGCAAATT GTTTACCTCA 4620
GAGTTGGGTG TCACAGAACA TGTTGAAGGA GACCCTTGCA AATTTGCACT GTGGGTGGGG 4680
AGAACACCAA CTTCAGATAA TAAAATTGTC CTTAAGGCTT CCAGCATAGA GAACAAGCAG 4740
GACTGGATAA AGCATATCCG CGAAGTCATC CAGGAGCGGA CGATCCACCT GAAGGGAGCC 4800
CTGAAGGAGC CCATTCACAT CCCTAAGACC GCTCCCGCCA CAAGACAGAA GGGAAGGAGG 4860
GATGGAGAGG ATCTGGACAG CCAAGGAGAC GGCAGCAGCC AGCCTGATAC GATTTCCATC 4920
GCCTCACGGA CGTCTCAGAA CACGCTGGAC AGCGATAAG/G TGTCCTGCCT GAAGGAGCTG 4980
GTGGCCCGAG TGCTGCAGAG GCTGTGCGAG CGCGGCGCGA GAACGTGCT GGCCTTCGGC 5040
TTCGCGCTGC TGGACGGGGC CCGCGGGGC CCCCCCGAGG CCTTCACCAC CAGCGTGCGC 5100
AGCTACCTGC CCAACACGGT GACCGACGCA CTGCGGGGGA GCGGGGCGTG GGGGCTGCTG 5160
CTGCGCCGCG TGGGCGACGA CGTGCTGGTT CACCTGCTGG CACGCTGCGC GCTCTTTGTG 5220
CTGGTGGCTC CCAGCTGCGC CTACCAGGTG TGCGGGCCGC CGCTGTACCA GCTCGGCGCT 5280
GCCACTCAGG CCCGGCCCCC GCCACACGCT AGTGGACCCC GAAGGCGTCT GGGATGCGAA 5340
CGGGCCTGGA ACCATAGCGT CAGGGAGGCC GGGGTCCCCC TGGGCCTGCC AGCCCCGGGT 5400
GCGAGGAGGC GCGGGGGCAG TGCCAGCCGA AGTCTGCCGT TGCCCAAGAG GCCCAGGCGT 5460
GGCGCTGCCC CTGAGCCGGA GCGGACGCCC GTTGGGCAGG GGTCCTGGGC CCACCCGGGC 5520
AGGACGCGTG GACCGAGTGA CCGTGGTTTC TGTGTGGTGT CACCTGCCAG ACCCGCCGAA 5580
GAAGCCACCT CTTTGGAGGG TGCGCTCTCT GGCACGCGCC ACTCCCACCC ATCCGTGGGC 5640
CGCCAGCACC ACGCGGGCCC CCCATCCACA TCGCGGCCAC CACGTCCCTG GGACACGCCT 5700
TGTCCCCCGG TGTACGCCGA GACCAAGCAC TTCCTCTACT CCTCAGGCGA CAAGGAGCAG 5760
CTGCGGCCCT CCTTCCTACT CAGCTCTCTG AGGCCCAGCC TGACTGGCGC TCGGAGGCTC 5820
GTGGAGACCA TCTTTCTGGG TTCCAGGCCC TGGATGCCAG GGACTCCCCG CAGGTTGCCC 5880
CGCCTGCCCC AGCGCTACTG GCAAATGCGG CCCCTGTTTC TGGAGCTGCT GGGAACCAC 5940
GCGCAGTGCC CCTACGGGGT GCTCCTCAAG ACGCACTGCC CGCTGCGAGC TGCGGTCACC 6000
CCAGCAGCCG GTGTCTGTGC CCGGGAGAAG CCCCAGGGCT CTGTGGCGGC CCCCGAGGAG 6060
GAGGACACAG ACCCCCGTCG CCTGGTGCAG CTGCTCCGCC AGCACAGCAG CCCCTGGCAG 6120
```

FIG. 1C

```
GTGTACGGCT TCGTGCGGGC CTGCCTGCGC CGGCTGGTGC CCCCAGGCCT CTGGGGCTCC    6180
AGGCACAACG AACGCCGCTT CCTCAGGAAC ACCAAGAAGT TCATCTCCCT GGGGAAGCAT    6240
GCCAAGCTCT CGCTGCAGGA GCTGACGTGG AAGATGAGCG TGCGGGACTG CGCTTGGCTG    6300
CGCAGGAGCC CAGGGGTTGG CTGTGTTCCG GCCGCAGAGC ACCGTCTGCG TGAGGAGATC    6360
CTGGCCAAGT TCCTGCACTG GCTGATGAGT GTGTACGTCG TCGAGCTGCT CAGGTCTTTC    6420
TTTTATGTCA CGGAGACCAC GTTTCAAAAG AACAGGCTCT TTTTCTACCG GAAGAGTGTC    6480
TGGAGCAAGT TGCAAAGCAT TGGAATCAGA CAGCACTTGA AGAGGGTGCA GCTGCGGGAG    6540
CTGTCGGAAG CAGAGGTCAG GCAGCATCGG GAAGCCAGGC CCGCCCTGCT GACGTCCAGA    6600
CTCCGCTTCA TCCCCAAGCC TGACGGGCTG CGGCCGATTG TGAACATGGA CTACGTCGTG    6660
GGAGCCAGAA CGTTCCGCAG AGAAAAGAGG GCCGAGCGTC TCACCTCGAG GGTGAAGGCA    6720
CTGTTCAGCG TGCTCAACTA CGAGCGGGCG CGGCGCCCCG GCCTCCTGGG CGCCTCTGTG    6780
CTGGGCCTGG ACGATATCCA CAGGGCCTGG CGCACCTTCG TGCTGCGTGT GCGGGCCCAG    6840
GACCCGCCGC CTGAGCTGTA CTTTGTCAAG GTGGATGTGA CGGGCGCGTA CGACACCATC    6900
CCCCAGGACA GGCTCACGGA GGTCATCGCC AGCATCATCA AACCCCAGAA CACGTACTGC    6960
GTGCGTCGGT ATGCCGTGGT CCAGAAGGCC GCCCATGGGC ACGTCCGCAA GGCCTTCAAG    7020
AGCCACGTCT CTACCTTGAC AGACCTCCAG CCGTACATGC GACAGTTCGT GGCTCACCTG    7080
CAGGAGACCA GCCCGCTGAG GGATGCCGTC GTCATCGAGC AGAGCTCCTC CCTGAATGAG    7140
GCCAGCAGTG GCCTCTTCGA CGTCTTCCTA CGCTTCATGT GCCACCACGC CGTGCGCATC    7200
AGGGGCAAGT CCTACGTCCA GTGCCAGGGG ATCCCGCAGG GCTCCATCCT CTCCACGCTG    7260
CTCTGCAGCC TGTGCTACGG CGACATGGAG AACAAGCTGT TTGCGGGGAT TCGGCGGGAC    7320
GGGCTGCTCC TGCGTTTGGT GGATGATTTC TTGTTGGTGA CACCTCACCT CACCCACGCG    7380
AAAACCTTCC TCAGGACCCT GGTCCGAGGT GTCCCTGAGT ATGGCTGCGT GGTGAACTTG    7440
CGGAAGACAG TGGTGAACTT CCCTGTAGAA GACGAGGCCC TGGGTGGCAC GGCTTTTGTT    7500
CAGATGCCGG CCCACGGCCT ATTCCCCTGG TGCGGCCTGC TGCTGGATAC CCGGACCCTG    7560
GAGGTGCAGA GCGACTACTC CAGCTATGCC CGGACCTCCA TCAGAGCCAG TCTCACCTTC    7620
AACCGCGGCT TCAAGGCTGG GAGGAACATG CGTCGCAAAC TCTTTGGGGT CTTGCGGCTG    7680
AAGTGTCACA GCCTGTTTCT GGATTTGCAG GTGAACAGCC TCCAGACGGT GTGCACCAAC    7740
ATCTACAAGA TCCTCCTGCT GCAGGCGTAC AGGTTTCACG CATGTGTGCT GCAGCTCCCA    7800
TTTCATCAGC AAGTTTGGAA GAACCCCACA TTTTTCCTGC GCGTCATCTC TGACACGGCC    7860
TCCCTCTGCT ACTCCATCCT GAAAGCCAAG AACGCAGGGA TGTCGCTGGG GGCCAAGGGC    7920
GCCGCCGGCC CTCTGCCCTC CGAGGCCGTG CAGTGGCTGT GCCACCAAGC ATTCCTGCTC    7980
AAGCTGACTC GACACCGTGT CACCTACGTG CCACTCCTGG GGTCACTCAG GACAGCCCAG    8040
ACGCAGCTGA GTCGGAAGCT CCCGGGGACG ACGCTGACTG CCCTGGAGGC CGCAGCCAAC    8100
CCGGCACTGC CCTCAGACTT CAAGACCATC CTGGACTGA                           8139
```

(SEQ ID NO:1)

FIG. 2

```
MSGSSGGAAA PAASSGPAAA ASAAGSGCGG GAGEGAEEAA KDLADIAAFF RSGFRKNDEM  60
KAMDVLPILK EKVAYLSGGR DKRGGPILTF PARSNHDRIR QEDLRRLISY LACIPSEEVC 120
KRGFTVIVDM RGSKWDSIKP LLKILQESFP CCIHVALIIK PDNFWQKQRT NFGSSKFEFE 180
TNMVSLEGLT KVVDPSQLTP EFDGCLEYNH EEWIEIRVAF EDYISNATHM LSRLEELQDI 240
LAKKELPQDL EGARNMIEEH SQLKKKVIKA PIEDLDLEGQ KLLQRIQSSE SFPKKNSGSG 300
NADLQNLLPK VSTMLDRLHS TRQHLHQMWH VRKLKLDQCF QLRLFEQDAE KMFDWITHNK 360
GLFLNSYTEI GTSHPHAMEL QTQHNHFAMN CMNVYVNINR IMSVANRLVE SGHYASQQIR 420
QIASQLEQEW KAFAAALDER STLLDMSSIF HQKAEKYMSN VDSWCKACGE VDLPSELQDL 480
EDAIHHHQGI YEHITLAYSE VSQDGKSLLD KLQRPLTPGS SDSLTASANY SKAVHHVLDV 540
IHEVLHHQRQ LENIWQHRKV RLHQRLQLCV FQQDVQQVLD WIENHGEAFL SKHTGVGKSL 600
HRARALQKRH EDFEEVAQNT YTNADKLLEA AEQLAQTGEC DPEEIYQAAH QLEDRIQDFV 660
RRVEQRKILL DMSVSFHTHV KELWTWLEEL QKELLDDVYA ESVEAVQDLI KRFGQQQQTT 720
LQVTVNVIKE GEDLIQQLRD SAISSNKTPH NSSINHIETV LQQLDEAQSQ MEELFQERKI 780
KLELFLQLRI FERDAIDIIS DLESWNDELS QQMNDFDTED LTIAEQRLQH HADKALTMNN 840
LTFDVIHQGQ DLLQYVNEVQ ASGVELLCDR DVDMATRVQD LLEFLHEKQQ ELDLAAEQHR 900
KHLEQCVQLR HLQAEVKQVL GWIRNGESML NAGLITASSL QEAEQLQREH EQFQHAIEKT 960
HQSALQVQQK AEAMLQANHY DMDMIRDCAE KVASHWQQLM LKMEDRLKLV NASVAFYKTS 1020
EQVCSVLESL EQEYKREEDW CGGADKLGPN SETDHVTPMI SKHLEQKEAF LKACTLARRN 1080
ADVFLKYLHR NSVNMPGMVT HIKAPEQQVK NILNELFQRE NRVLHYWTMR KRRLDQCQQY 1140
VVFERSAKQA LEWIHDNGEF YLSTHTSTGS SIQHTQELLK EHEEFQITAK QTKERVKLLI 1200
QLADGFCEKG HAHAAEIKKC VTAVDKRYRD FSLRMEKYRT SLEKALGISS DSNKSSKSLQ 1260
LDIIPASIPG SEVKLRDAAH ELNEEKRKSA RRKEFIMAEL IQTEKAYVRD LRECMDTYLW 1320
EMTSGVEEIP PGIVNKELII FGNMQEIYEF HNNIFLKELE KYEQLPEDVG HCFVTWADKF 1380
QMYVTYCKNK PDSTQLILEH AGSYFDEIQQ RHGLANSISS YLIKPVQRIT KYQLLLKELL 1440
TCCEEGKGEI KDGLEVMLSV PKRANDAMHL SMLEGFDENI ESQGELILQE SFQVWDPKTL 1500
IRKGRERHLF LFEMSLVFSK EVKDSSGRSK YLYKSKLFTS ELGVTEHVEG DPCKFALWVG 1560
RTPTSDNKIV LKASSIENKQ DWIKHIREVI QERTIHLKGA LKEPIHIPKT APATRQKGRR 1620
DGEDLDSQGD GSSQPDTISI ASRTSQNTLD SDK/VSCLKEL VARVLQRLCE RGAKNVLAFG 1680
FALLDGARGG PPEAFTTSVR SYLPNTVTDA LRGSGAWGLL LRRVGDDVLV HLLARCALFV 1740
LVAPSCAYQV CGPPLYQLGA ATQARPPPHA SGPRRRLGCE RAWNHSVREA GVPLGLPAPG 1800
ARRRGGSASR SLPLPKRPRR GAAPEPERTP VGQGSWAHPG RTKGPSDRGF CVVSPARPAE 1860
EATSLEGALS GTREHSPSVG RQHHAGPPST SRPPRPWDTP CPPVYAETKH FLYSSGDKEQ 1920
LRPSFLLSSL RPSLTGARRL VETIFLGSRP WMPGTPRRLP RLPQRYWQMR PLFLELLGNH 1980
AQCPYGVLLK THCPLRAAVT PAAGVCAREK PQGSVAAPEE EDTDPRRLVQ LLRQHSSPWQ 2040
VYGFVRACLR RLVPPGLWGS RHNERRFLRN TKKFISLGKH AKLSLQELTW KMSVRDCAWL 2100
RRSPGVGCVP AAEHRLREEI LAKFLHWLMS VYVVELLRSF FYVTETTFQK NRLFFYRKSV 2160
WSKLQSIGIR QHLKRVQLRE LSEAEVRQHR EARPALLTSR LRFIPKPDGL RPIVNMDYVV 2220
GARTFRREKR AERLTSRVKA LFSVLNYERA RRPGLLGASV LGLDDIHRAW RTFVLRVRAQ 2280
DPPPELYFVK VDVTGAYDTI PQDRLTEVIA SIIKPQNTYC VRRYAVVQKA AHGHVRKAFK 2340
SHVSTLTDLQ PYMRQFVAHL QETSPLRDAV VIEQSSSLNE ASSGLFDVFL RFMCHHAVRI 2400
RGKSYVQCQG IPQGSILSTL LCSLCYGDME NKLFAGIRRD GLLLRLVDDF LLVTPHLTHA 2460
KTFLRTLVRG VPEYGCVVNL RKTVVNFPVE DEALGGTAFV QMPAHGLFPW CGLLLDTRTL 2520
EVQSDYSSYA RTSIRASLTF NRGFKAGRNM RRKLFGVLRL KCHSLFLDLQ VNSLQTVCTN 2580
IYKILLLQAY RFHACVLQLP FHQQVWKNPT FFLRVISDTA SLCYSILKAK NAGMSLGAKG 2640
AAGPLPSEAV QWLCHQAFLL KLTRHRVTYV PLLGSLRTAQ TQLSRKLPGT TLTALEAAAN 2700
PALPSDFKTI LD                                                    2712
```

(SEQ ID NO:2)

US 10,370,723 B2

TERT FUSIONS

CLAIM OF PRIORITY

This application is a national stage application of and claims priority under 35 U.S.C. § 371 to International Application No. PCT/US2015/040557, filed Jul. 15, 2015, which claims the benefit of U.S. Provisional Application No. 62/025,872, filed Jul. 17, 2014, the contents of both of which are incorporated herein by reference in their entirety to provide continuity of disclosure.

The instant application contains a Sequence Listing which has been submitted electronically in ASCII format and is hereby incorporated by reference in its entirety. Said ASCII copy, created on Sep. 17, 2015, is named 12386.0008-00304_SL.txt and is 35,024 bytes in size.

This invention relates to TERT (telomerase reverse transcriptase) gene fusions and TERT fusion proteins. The invention further relates to methods of diagnosing diseases or disorders associated with TERT fusions, such as conditions mediated by TERT activity, or conditions associated with aberrant TERT expression or activity, or overexpression of TERT.

Many forms of cancer are caused by genetic lesions that give rise to tumor initiation and growth. Genetic lesions may include chromosomal aberrations, such as translocations, inversions, deletions, copy number changes, gene expression level changes, and somatic and germline mutations. Indeed, the presence of such genomic aberrations is a hallmark feature of many cancers, including, for example, B cell cancer, lung cancer, breast cancer, ovarian cancer, pancreatic cancer, and colon cancer. In some models, cancer represents the phenotypic end-point of multiple genetic lesions that endow cells with a full range of biological properties required for tumorigenesis.

Recent efforts by The Cancer Genome Atlas (TCGA), the International Cancer Genome Consortium (ICGC), and dozens of other large-scale profiling efforts have generated an enormous amount of new sequencing data for dozens of cancer types—this includes whole-genome DNA, whole-exome DNA, and full-transcriptome RNA sequencing. These efforts have led to the identification of new driver genes and fusion genes within multiple cancer types. Fusions, particularly fusions involving kinases, are of particular interest, as such fusions have been shown to be oncogenic, and have been successfully targeted by new therapeutics. For example, anaplastic lymphoma kinase (ALK), one of the receptor tyrosine kinases, is known to become oncogenic when fused with various genes. See. e.g., M. Soda et al, "Identification of the transforming EML4-ALK fusion gene in non-small-cell lung cancer." *Nature* 444:561-566 (2007).

A need exists for identifying novel genetic lesions associated with cancer. For example, the presence of fusions involving a gene in samples collected from more than one source can indicate that the gene is an oncogenic driver. The identification of such fusions can be an effective approach to diagnosis of cancers and development of compounds, compositions, methods, and assays for evaluating and treating cancer patients.

In one aspect, the invention provides methods for detecting the presence of a TERT fusion in a biological sample. The methods include the steps of: (a) obtaining a biological sample from a mammal; and (b) contacting the sample with a reagent that detects a TERT fusion, to determine whether a TERT fusion is present in the biological sample. In some embodiments, the sample can be from, e.g., a cancer patient, such as, e.g., a patient having sarcoma. In some embodiments, the fusion can be, e.g., a TRIO:TERT fusion. In some embodiments, the TRIO:TERT fusion has all or a part of the nucleotide and/or amino acid sequence (such as, e.g., the fusion junction) set forth in SEQ ID NO:1 and SEQ ID NO:2, respectively.

In another aspect, the invention provides methods of diagnosing a patient having a disease or disorder associated with aberrant TERT expression or activity, or overexpression of TERT; the methods include: (a) obtaining a biological sample from the patient; and (b) contacting the sample with a reagent that detects a TERT fusion to determine whether a TERT fusion is present in the biological sample, whereby the detection of the TERT fusion indicates the presence of a disorder associated with aberrant TERT expression or activity, or overexpression of TERT.

BRIEF DESCRIPTION OF THE FIGURES

FIGS. 1A, 1B, and 1C depict the nucleotide sequence of a TRIO:TERT gene fusion (SEQ ID NO:1) comprising a portion of the TRIO gene (NM_007118) up to and including exon 33 and a portion of the TERT gene (NM_198253) starting at exon 2. The underlined codons at nucleotides 4957-4959 and 4960-4962 encode the last amino acid of TRIO and the first amino acid of TERT, respectively. The slash after nucleotide 4959 indicates the breakpoint (fusion junction) where translocation and in-frame fusion has occurred.

FIG. 2 depicts the amino acid sequence of a TRIO:TERT fusion protein (SEQ ID NO:2). The slash between amino acids 1653 and 1654 indicates the breakpoint or fusion junction between the TRIO and TERT proteins. Amino acids 1653 and 1654 correspond to nucleotides 4957-4959 and 4960-4962 in SEQ ID NO: 1, respectively.

EXEMPLARY EMBODIMENTS OF THE INVENTION

Figure 3:
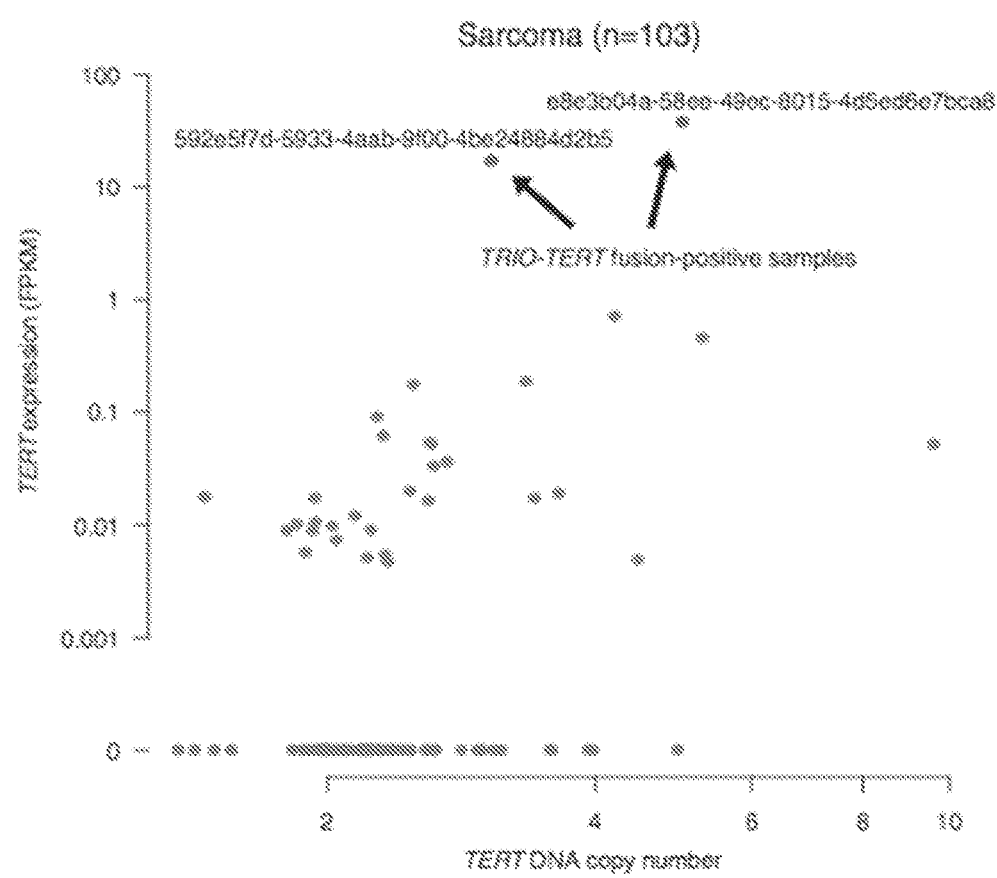
FIG. 3 is a graph showing TERT DNA copy number versus the mRNA expression in sarcoma samples.

The invention is based, at least in part, on the discovery of novel recombination or translocation events in cancer patients that result in at least a fragment of a TERT gene linked to a non-homologous promoter via a recombination or translocation event that may result in aberrant expression (e.g., in a location where TERT is not typically expressed) or overexpression of the reverse transcriptase (RT) domain of the TERT gene and thus, an increase in RT activity. Thus, a new patient population is identified, which is characterized by the presence of a TERT fusion, e.g., a TERT gene fusion or fusion protein. This new patient population suffers from or is susceptible to disorders mediated by aberrant TERT expression or activity, or overexpression of TERT, such as, e.g., a cancer. In another aspect of the invention, a new subtype of cancer is identified, which is characterized by the presence of the TERT fusions described herein. In some embodiments, the new patient population suffers from or is susceptible to a sarcoma characterized by the presence of a TERT fusion. New methods of diagnosing the patient population and the TERT fusion cancer subtype are also provided.

The term "TERT fusion" is used generically herein, and includes any fusion molecule (e.g., gene, gene product (e.g., cDNA, mRNA, or protein), and variants thereof) that includes a fragment of TERT, particularly the coding region for the RT domain of TERT, and a fragment of a second, non-homologous gene. In some embodiments, the coding sequence for the RT domain of TERT is under control of the promoter of the non-homologous gene. A TERT fusion protein generally includes the RT domain of TERT. In some embodiments, the TERT fusion is a TRIO:TERT fusion.

TERT Gene Fusions and Fusion Proteins

TERT is a catalytic subunit of the enzyme telomerase, which, together with the telomerase RNA component (TERC), comprises the most important unit of the telomerase complex. Telomerases are part of a distinct subgroup of RNA-dependent polymerases. Telomerase lengthens chromosomes' telomeres, thereby allowing senescent cells that would otherwise become postmitotic and undergo apoptosis to exceed the Hayflick limit and become potentially immortal, as is often the case with cancerous cells. TERT is responsible for catalyzing the addition of nucleotides in a TTAGGG sequence to the ends of a chromosome's telomeres. This addition of repetitive DNA sequences prevents degradation of the chromosomal ends following multiple rounds of replication. Telomerase expression plays a role in cellular senescence, as it is normally repressed in postnatal somatic cells, resulting in progressive shortening of telomeres. Telomere deficiency is often linked to aging, cancers, and the conditions dyskeratosis congenita (DKC) and Cri du chat. Meanwhile, overexpression of TERT is often associated with cancers and tumor formation. Telomerase activity is a hallmark of many cancers, and two other genetic mechanisms of TERT reactivation have been described previously; both somatic mutations in the promoter of the TERT gene and DNA copy number gains of TERT were shown to activate its transcription. See Huang, F. W. et al. "Highly recurrent TERT promoter mutations in human melanoma," *Science* 339: 957-959 (2013); see also Zhang, A. et al. "Frequent amplification of the telomerase reverse transcriptase gene in human tumors," *Cancer Res.* 60: 6230-6235 (2000).

The invention provides novel TERT fusions that are associated with different types of disorders. These findings provide a reasonable expectation that TERT fusions represent an alternative mechanism for telomerase reactivation in cancers. For example, the TERT fusions disclosed herein can be associated with certain cancers, such as, e.g., sarcoma. In some embodiments, the sarcoma associated with a TERT fusion is liposarcoma. In some embodiments, the TERT fusions disclosed herein can be associated with other disorders mediated by aberrant TERT expression or activity, or overexpression of TERT.

TERT gene fusions are generated by a fusion between at least a part of the TERT gene and a part of another gene as a result of a translocation (including inversion) within a chromosome or between chromosomes. As a result of a translocation, the TERT gene may be placed under the transcriptional control of the partner gene promoter, e.g., TRIO, resulting in aberrant TERT expression or activity, or overexpression of TERT. The overexpression can lead to certain cancers. As used herein, the 5'-region is upstream of, and the 3'-region is downstream of, a fusion junction or breakpoint in one of the component genes. TERT and the gene or protein that it is fused to are referred to as "fusion partners." Alternatively, they may be identified as a "TERT gene fusion" or a "TERT fusion protein," which are collectively termed "TERT fusions." The TERT fusions disclosed herein possess a RT activity. The phrase "having a RT activity" as used in this application means having an activity as an enzyme catalyzing the generation of complementary DNA (cDNA) from an RNA template, such as, e.g., having a telomerase RT activity, which means having an activity as an enzyme, when together with the telomerase RNA component (TERC), catalyzing the addition of nucleotides (e.g., a TTAGGG sequence) to the ends of a chromosome's telomeres.

In some exemplary embodiments, the fusion partner is all or a portion of the DNA or amino acid sequence for TRIO (trio Rho guanine nucleotide exchange factor). In certain embodiments of the invention, a fusion includes an in-frame fusion of all or a portion of the TRIO gene (e.g., a fragment of the TRIO gene comprising a TRIO promotor or a functional fragment thereof, and one or more exons encoding TRIO or a fragment thereof) and an portion of the TERT gene (e.g., one or more exons encoding the RT domain or a functional fragment thereof). Such a fusion can be referred to as a TRIO:TERT fusion. In one embodiment, the TRIO: TERT fusion comprises sufficient TERT sequence to drive expression of a fusion protein that has a RT activity. In some embodiments, the TRIO:TERT fusion drives expression of a fusion protein that has elevated TERT activity as compared with wild type TERT in the same tissue or cell. In some embodiments, the TRIO:TERT fusion drives expression of a fusion protein that confers a tissue or cell elevated RT activity as compared with a wild type tissue or cell without such a fusion. In some embodiments, the TRIO:TERT fusion comprises the non-catalytic portion of TRIO kinase, which resulted in the upregulation of the transcription of TERT.

In some embodiments, the invention provides a TRIO: TERT gene fusion comprising all or a portion of the nucleotide sequence depicted in FIG. 1A-1C (SEQ ID NO:1) that includes the fusion junction. SEQ ID NO:1 comprises TRIO (NM_007118) up to exon 33 fused to TERT (NM_198253), beginning at exon 2. In some embodiments, the TRIO:TERT gene fusion comprises a nucleotide sequence that is at least 85%, at least 90%, at least 95%, at least 97%, at least 98%, or at least 99% identical to all or part of SEQ ID NO:1 or its complement. Reference to "all or a portion" or "all or part" of a TRIO:TERT gene fusion, means that the nucleotide sequence comprises the entire TRIO:TERT gene fusion nucleotide sequence or a fragment of that sequence that comprises the fusion junction breakpoint point between TRIO and TERT. The fragment may comprise 7, 8, 9, 10, 12, 14, 16, 18, 20, 21, 22, 23, 24, 25, 26, 27, 28, 29, 30, 35, 40, 45, 50, 60, 70, 80, 90, 100, 120, 150, 175, 200, 250, 300, or more nucleotides spanning the fusion junction. An exemplary TRIO:TERT gene fusion junction is identified by a slash ("/") in FIG. 1B. Unless specified, a reference to all or part of SEQ ID NO:1 encompasses either the coding strand or the complementary strand, or both.

The nucleic acid sequences of TERT gene fusions may be used as probes, primers, or bait to identify nucleotides from a biological sample that include, flank, or hybridize to TERT fusions, such as TRIO:TERT (e.g., all or part of SEQ ID NO: 1), at, e.g., the fusion junctions. In certain embodiments, the probe, primer, and/or bait molecule is an oligonucleotide that allows capture, detection, or isolation of a TERT gene fusion in a biological sample. In certain embodiments, the probes or primers derived from the nucleic acid sequences of TERT gene fusions (e.g., from the fusion junctions) may be used, for example, for polymerase chain reaction (PCR) amplification. The oligonucleotide can comprise a nucleotide sequence substantially complementary to a fragment of the TERT gene fusion nucleic acid molecules described herein. The sequence identity between the nucleic acid fragment, e.g., the oligonucleotide and the target TERT gene fusion sequence, need not be exact, so long as the sequences are sufficiently complementary to allow the capture, detection, and/or isolation of the target sequence. In one embodiment, the nucleic acid fragment is a probe or primer that includes an oligonucleotide between about 5 and 25, e.g., between 10 and 20, or 10 and 15 nucleotides in length that includes the fusion junction of a TERT fusion, such as, e.g., TRIO:TERT (e.g., all or part of SEQ ID NO: 1). In other embodiments, the nucleic acid fragment is a bait that includes an oligonucleotide between about 100 to 300 nucleotides, 130 and 230 nucleotides, or 150 and 200 nucleotides in length that includes the fusion junction of a TERT gene fusion, such as, e.g., TRIO:TERT (e.g., all or part of SEQ ID NO: 1).

In certain embodiments, the nucleic acid fragments hybridize to a nucleotide sequence that includes a breakpoint or fusion junction, e.g., a breakpoint or fusion junction as identified by a slash ("/") in FIG. 1B. For example, the nucleic acid fragment can hybridize to a nucleotide sequence that includes the fusion junction between the TRIO transcript and the TERT transcript (e.g., nucleotides 4957-4962 of SEQ ID NO:1), e.g., a nucleotide sequence that includes all or a portion of SEQ ID NO:1. In exemplary embodiments, the nucleic acid fragments include or hybridize to a nucleotide sequence within exons 1-33 of a TRIO gene and exons 2-16 of a TERT gene (e.g., a portion of SEQ ID NO:1 comprising nucleotides 4957-4962, 4955-4964, 4950-4969, 4935-4984, or 4910-5009).

In other embodiments, the nucleic acid fragment includes a bait that comprises a nucleotide sequence that hybridizes to a TERT gene fusion nucleic acid molecule described herein, and thereby allows the detection, capture, and/or isolation of the nucleic acid molecule. In one embodiment, a bait is suitable for solution phase hybridization. In other embodiments, a bait includes a binding entity or detection entity, e.g., an affinity tag or fluorescent label, that allows detection, capture, and/or separation, e.g., by binding to a binding entity, of a hybrid formed by a bait and a nucleic acid hybridized to the bait.

In exemplary embodiments, the nucleic acid fragments used as bait hybridize to a nucleotide sequence that includes a fusion junction between the TRIO transcript and the TERT transcript, e.g, a nucleotide sequence within SEQ ID NO:1 comprising nucleotides 4957-4962 (such as, e.g., a sequence comprising nucleotides 4955-4964, 4950-4969, 4935-4984, or 4910-5009 of SEQ ID NO: 1).

The nucleic acid fragments can be detectably labeled with, e.g., a radiolabel, a fluorescent label, a bioluminescent label, a chemiluminescent label, an enzyme label, a binding pair label (e.g., biotin/streptavidin), an antigen label, or can include an affinity tag or identifier (e.g., an adaptor, a barcode, or other sequence identifier). Labeled or unlabeled nucleic acids and/or nucleic acid fragments may be used in reagents for detecting, capturing, or isolating TERT gene fusions, such as, e.g., TRIO:TERT (for example, all or part of SEQ ID NO: 1).

Another aspect of the invention provides TERT fusion proteins (such as, e.g., a purified or isolated TRIO:TERT fusion protein), biologically active or antigenic fragments thereof, and use of those polypeptides for detecting the biological activity (such as tumorigenic activity) of a TERT fusion protein. Exemplary embodiments of the TERT fusion protein is a TRIO:TERT fusion protein that comprises all or part of the amino acid sequence set forth in SEQ ID NO:2 that includes the fusion junction. In some embodiments, the TRIO:TERT gene fusion encodes a protein having a sequence that is at least 85%, at least 90%, at least 95%, at least 97%, at least 98%, or at least 99% identical to all or part of the sequence depicted in FIG. 2 (SEQ ID NO:2). Reference to "all or a portion" or "all or part" of a TERT fusion protein, means an amimo acid sequence that comprises the entire TERT fusion protein amino acid sequence or a fragment of that sequence that comprises the fusion junction breakpoint point between TERT and its fusion partner, e.g., TRIO. The fragment may comprise 8, 10, 12, 14, 15, 16, 18, 20, 21, 22, 23, 24, 25, 26, 27, 28, 29, 30, 35, 40, 45, 50, 75, or more amino acids spaning the fusion junction. An example of a specific TRIO:TERT fusion protein junction is identified by a slash ("/") in FIG. 2.

In other embodiments, the TERT fusion protein of the invention can include a fragment of a TRIO protein and a fragment of a TERT protein. In one embodiment, the TERT fusion protein is a TRIO:TERT fusion protein having the amino acid sequence of SEQ ID NO:2 or a fragment thereof that includes the fusion junction, such as, e.g., amino acids 1649-1658, 1644-1663, or 1629-1678 of SEQ ID NO:2. In some embodiments, the TERT fusion protein is a TRIO:TERT fusion protein comprising an amino acid sequence that is at least 85%, at least 90%, at least 95%, at least 97%, at least 98%, or at least 99% identical to SEQ ID NO:2 or a fragment thereof (e.g., amino acids 1649-1658, 1644-1663, or 1629-1678 of SEQ ID NO:2).

In certain embodiments, the TERT fusion protein includes a functional RT domain. In some embodiments, the TERT fusion protein results in elevated TERT activity (e.g., elevated activity in a cancer cell) as compared with wild type TERT activity (e.g., in a cancer cell, a non-cancer cell adjacent to the cancer cell, or a non-cancer cell from a control sample, such as a cancer free subject). In one exemplary embodiment, the TERT fusion protein is a TRIO:TERT fusion and includes a TERT RT domain or a functional fragment thereof.

In another embodiment, the TERT fusion protein or fragment is a peptide, e.g., an immunogenic peptide or protein, that contains a fusion junction with a heterologous protein as described herein. Such immunogenic peptides or proteins can be used for vaccine preparation for use in the treatment or prevention of cancers caused by or exacerbated by TERT gene fusions and TERT fusion proteins. In other embodiments, such immunogenic peptides or proteins can be used to raise antibodies specific to the fusion protein. In some embodiments, the TERT fusion protein is present in combination with or is further conjugated to one or more adjuvant(s) or immunogen(s), e.g., a protein capable of enhancing an immune response to the TERT fusion protein (e.g., a hapten, a toxoid, etc.). In some embodiments, the TERT fusion protein is a TRIO:TERT fusion protein. In some embodiments, the TERT fusion protein comprises the fusion junction of SEQ ID NO:2.

Thus, another aspect of the invention provides an antibody that binds to a TERT fusion protein (such as, e.g., a TRIO:TERT fusion protein) or a fragment thereof. In certain embodiments, the antibody recognizes a TERT fusion protein but does not recognize wild type TERT or the wild type fusion partner (such as, e.g., TRIO). In some embodiments, the antibody binds to an epitope comprising the junction between TERT and the fusion partner (e.g., the junction of TRIO:TERT). In one embodiment, the antibody binds to a TRIO:TERT fusion protein having the amino acid sequence of SEQ ID NO:2 or a fragment thereof, such as, e.g., amino acids 1649-1658, 1644-1663, or 1629-1678 of SEQ ID NO:2.

In certain embodiments, the antibodies of the invention inhibit and/or neutralize the biological activity of the TERT fusion protein, and more specifically, in some embodiments, the kinase activity of the TERT fusion protein. In other embodiments, the antibodies may be used to detect a TERT fusion protein or to diagnose a patient suffering from a disease or disorder associated with the expression of a TERT fusion protein Detection and Diagnostic Methods In another aspect, the invention provides a method of detecting the presence of a TERT gene fusion or fusion protein, such as, e.g., a TRIO:TERT fusion as described herein. The presence of a TERT gene fusion indicates that the mammal providing the biological sample suffers from or is at risk of developing a disorder mediated by aberrant TERT expression or activity, or overexpression of TERT, such as, e.g., a cancer. The presence of a TERT gene fusion may also indicate that the disorder is treatable with a TERT fusion inhibitor. In some embodiments the cancer is associated with aberrant TERT expression or activity, or overexpression of TERT. In some embodiments, the cancer is sarcoma. In some embodiments, the cancer is liposarcoma. In some embodiments, the TERT fusion present in the sample is TRIO:TERT and the cancer to be treated is sarscroma, e.g., liposarcoma.

In one embodiment, the TERT fusion detected is a nucleic acid molecule or a polypeptide. The method includes detecting whether a TERT fusion nucleic acid molecule or polypeptide is present in a cell (e.g., a circulating cell or a cancer cell), a tissue (e.g., a tumor), or a sample, e.g., a tumor sample, from a subject. In one embodiment, the sample is a nucleic acid sample. In one embodiment, the nucleic acid sample comprises DNA, e.g., genomic DNA or cDNA, or RNA, e.g., mRNA. In other embodiments, the sample is a protein sample.

The sample can be chosen from one or more sample types, such as, for example, tissue, e.g., cancerous tissue (e.g., a tissue biopsy), whole blood, serum, plasma, buccal scrape, sputum, saliva, cerebrospinal fluid, urine, stool, circulating tumor cells, circulating nucleic acids, or bone marrow.

I. Methods for Detecting Gene Fusions

In certain embodiments, the sample is acquired from a subject having or at risk of having a cancer (e.g., a patient), or alternatively, the method further includes acquiring a sample from the subject. In some embodiments, the TERT fusion is detected in a nucleic acid molecule by one or more methods chosen from: e.g., nucleic acid hybridization assay (e.g. in situ hybridization, comparative genomic hybridization, microarray, Southern blot, northern blot), amplification-based assays (e.g., PCR, PCR-RFLP assay, or real-time PCR), sequencing and genotyping (e.g. sequence-specific primers, high-performance liquid chromatography, or mass-spectrometric genotyping), and screening analysis (including metaphase cytogenetic analysis by karyotype methods.

(1) Hybridization Methods

In some embodiments, the reagent hybridizes to a TERT gene fusion, such as, e.g., nucleotides 4957-4962, 4955-4964, 4950-4969, 4935-4984, or 4910-5009 of SEQ ID NO:1. In one embodiment, the method includes: contacting a nucleic acid sample, e.g., a genomic DNA sample (e.g., a chromosomal sample or a fractionated, enriched or otherwise pre-treated sample) or a gene product (e.g., mRNA, or cDNA), obtained from the subject, with a nucleic acid fragment. e.g., a probe or primer as described herein (e.g., an exon-specific or a breakpoint-specific probe or primer), under conditions suitable for hybridization, and determining the presence or absence of the TERT gene fusion, such as, e.g. a TRIO:TERT gene fusion. In an alternate embodiment, the method includes the steps of obtaining a sample; exposing the sample to a nucleic acid probe which hybridizes to an mRNA or cDNA encoding a TERT fusion protein that comprises amino acids 1649-1658, 1644-1663, or 1629-1678 of SEQ ID NO:2

Hybridization, as described throughout the specification, may be carried out under stringent conditions, e.g., medium or high stringency. See. e.g., J. Sambrook, E. F. Fritsch, and T. Maniatis, *Molecular Cloning: A Laboratory Manual*, Cold Spring Harbor Laboratory Pr; 2nd edition (1989); T. Brown, *Hybridization Analysis of DNA Blots. Current Protocols in Molecular Biology* at 21:2.10.1-2.10.16 (2001). High stringency conditions for hybridization refer to conditions under which two nucleic acids must possess a high degree of base pair homology to each other in order to hybridize. Examples of highly stringent conditions for hybridization include hybridization in 4×sodium chloride/sodium citrate (SSC), at 65 or 70° C., or hybridization in 4×SSC plus 50% formamide at about 42 or 50° C., followed by at least one, at least two, or at least three washes in 1×SSC, at 65 or 70° C. Another example of highly stringent conditions includes hybridization in 2×SSC; 10×Denhardt solution (Fikoll 400+PEG+BSA; ratio 1:1:1); 0.1% SDS; 5 mM EDTA; 50 mM $Na_2HPO_4$; 250 µg/ml of herring sperm DNA; 50 µg/ml of tRNA; or 0.25 M of sodium phosphate buffer, pH 7.2; 1 mM EDTA7% SDS at 60° C.; followed by washing 2×SSC, 0.1% SDS at 60° C.

In some embodiments, the nucleic acid fragments can be detectably labeled with, e.g., a radiolabel, a fluorescent label, a bioluminescent label, a chemiluminescent label, an enzyme label, a binding pair label (e.g., biotin/streptavidin), an antigen-label, or can include an affinity tag or identifier (e.g., an adaptor, barcode or other sequence identifier). Labeled or unlabeled nucleic acids and/or nucleic acid fragments may be used in reagents for detecting, capturing, or isolating TERT gene fusions. Labeled or unlabeled nucleic acids and/or nucleic acid fragments may be used in reagents for detecting, capturing, and/or isolating TERT gene fusions, such as, e.g., TRIO:TERT (e.g., all or part of SEQ ID NO: 1). In some embodiments, the labeled nucleic acid fragments can be detected using, e.g., autoradiography, microscopy (e.g., brightfield, fluorescence, or electron microscopy), enzyme-linked immunosorbent assay (ELISA), or immunohistochemistry.

In some embodiments, the method of determining the presence of a TERT gene fusion (such as, e.g., TRIO:TERT, as disclosed herein) in a mammal comprises the steps of obtaining a biological sample of the mammal (such as, e.g., from a human cancer); exposing the sample to a nucleic acid probe which hybridizes to a DNA which comprises a TERT gene fusion; wherein hybridization of the probe to the DNA in the sample indicates the presence of a TERT gene fusion in the mammal. In some embodiments, the human cancer is sarcoma. In some embodiments, the human cancer is liposarcoma.

In some embodiments, the method comprises performing chromosome in situ hybridization with chromosomal DNA from a biological sample to detect the presence of a TERT gene fusion (such as, e.g., TRIO:TERT, as disclosed herein). In some embodiments, the chromosome in situ hybridization comprises the steps of: providing a chromosome (e.g., interphase or metaphase chromosome) preparation (e.g., by attaching the chromosomes to a substrate (e.g., glass)); denaturing the chromosomal DNA (e.g., by exposure to formamide) to separate the double strands of the polynucleotides from each other; exposing the nucleic acid probe to the chromosomes under conditions to allow hybridization of the probe to the target DNA; removing unhybridized or non-specifically hybridized probes by washing; and detecting the hybridization of the probe with the target DNA. In some embodiments, the chromosome in situ hybridization is fluorescence in situ hybridization (FISH). In some embodiments, the probe is labeled directly by a fluorescent label, or indirectly by incorporation of a nucleotide containing a tag or reporter molecule (e.g., biotin, digoxigenin, or hapten) which after hybridization to the target DNA is then bound by fluorescently labeled affinity molecule (e.g., an antibody or streptavidin). In some embodiments, the hybridization of the probe with the target DNA in FISH can be visualized using a fluorescence microscope.

In other embodiments, the method comprises performing Southern blot with DNA polynucleotides from a biological sample to detect the presence of a TERT gene fusion (such as, e.g., TRIO:TERT, as disclosed herein). In some embodiments, the Southern blot comprises the steps of: optionally fragmenting the polynucleotides into smaller sizes by restriction endonucleases; separating the polynucleotides by gel electrophoresis; denaturing the polynucleotides (e.g., by heat or alkali treatment) to separate the double strands of the polynucleotides from each other; transferring the polynucleotides from the gel to a membrane (e.g., a nylon or nitrocellulose membrane); immobilizing the polynucleotides to the membrane (e.g., by UV light or heat); exposing the nucleic acid probe to the polynucleotides under conditions to allow hybridization of the probe to the target DNA; removing unhybridized or non-specifically hybridized probes by washing; and detecting the hybridization of the probe with the target DNA.

(2) Amplification-Based Assays

In certain embodiments, the method of determining the presence of a TERT gene fusion, comprises (a) performing a PCR amplification reaction with polynucleotides from a biological sample, wherein the amplification reaction utilizes a pair of primers which will amplify at least a fragment of the TERT gene fusion, wherein the fragment comprises the fusion junction, wherein the first primer is in sense orientation and the second primer is in antisense orientation; and (b) detecting an amplification product, wherein the presence of the amplification product is indicative of the presence of a TERT fusion polynucleotide in the sample. In specific exemplary embodiments, the TERT gene fusion is TRIO:TERT, such as, e.g., the gene fusion of SEQ ID NO: 1 or a fragment thereof comprising nucleotides 4957-4962, 4955-4964, 4950-4969, 4935-4984, or 4910-5009 of SEQ ID NO:1

In some embodiments, step (a) of performing a PCR amplification reaction comprises: (i) providing a reaction mixture comprising the polynucleotides (e.g., DNA or cDNA) from the biological sample, the pair of primers which will amplify at least a fragment of the TERT gene fusion wherein the first primer is complementary to a sequence on the first strand of the polynucleotides and the second primer is complementary to a sequence on the second strand of the polynucleotides, a DNA polymerase, and a plurality of free nucleotides comprising adenine, thymine, cytosine, and guanine (dNTPs); (ii) heating the reaction mixture to a first predetermined temperature for a first predetermined time to separate the double strands of the polynucleotides from each other; (iii) cooling the reaction mixture to a second predetermined temperature for a second predetermined time under conditions to allow the first and second primers to hybridize with their complementary sequences on the first and second strands of the polynucleotides, and to allow the DNA polymerase to extend the primers; and (iv) repeating steps (ii) and (iii) for a predetermined number of cycles (e.g., 10, 15, 20, 25, 30, 35, 40, 45, or 50 cycles).

In some embodiments, the polynucleotides from the biological sample comprise RNA, and the method further comprises performing a RT-PCR amplification reaction with the RNA to synthesize cDNA as the template for subsequent or simultaneous PCR reactions. In some embodiments, the RT-PCR amplification reaction comprises providing a reaction mixture comprising the RNA, a primer which will amplify the RNA (e.g., a sequence-specific primer, a random primer, or oligo(dT)s), a reverse transcriptase, and dNTPs, and heating the reaction mixture to a third predetermined temperature for a third predetermined time under conditions to allow the reverse transcriptase to extend the primer.

(3) Sequencing and Genotyping

Another method for determining the presence of a TERT gene fusion molecule (such as, e.g., TRIO:TERT, as disclosed herein) includes: sequencing a portion of the nucleic acid molecule (e.g., sequencing the portion of the nucleic acid molecule that comprises the fusion junction of a TERT gene fusion), thereby determining that the TERT gene fusion is present in the nucleic acid molecule. Optionally, the sequence acquired is compared to a reference sequence, or a wild type reference sequence. In one embodiment, the sequence is determined by a next generation sequencing method. In some embodiments, the sequencing is automated and/or high-throughput sequencing. The method can further include acquiring, e.g., directly or indirectly acquiring, a sample, e.g., a tumor or cancer sample, from a patient.

In some embodiments, the sequencing comprises chain terminator sequencing (Sanger sequencing), comprising: providing a reaction mixture comprising a nucleic acid molecule from a biological sample, a primer complementary to a region of the template nucleic acid molecule, a DNA polymerase, a plurality of free nucleotides comprising adenine, thymine, cytosine, and guanine (dNTPs), and at least one chain terminating nucleotide (e.g., at least one di-deoxynucleotide (ddNTPs) chosen from ddATP, ddTTP, ddCTP, and ddGTP), wherein the at least one chain terminating nucleotide is present in a low concentration so that chain termination occurs randomly at any one of the positions containing the corresponding base on the DNA strand; annealing the primer to a single strand of the nucleic acid molecule; extending the primer to allow incorporation of the chain terminating nucleotide by the DNA polymerase to produce a series of DNA fragments that are terminated at positions where that particular nucleotide is used; separating the polynucleotides by electrophoresis (e.g., gel or capillary electrophoresis); and determining the nucleotide order of the template nucleic acid molecule based on the positions of chain termination on the DNA fragments. In some embodiments, the sequencing is carried out with four separate base-specific reactions, wherein the primer or the chain terminating nucleotide in each reaction is labeled with a separate fluorescent label. In other embodiments, the sequencing is carried out in a single reaction, wherein the four chain terminating nucleotides mixed in the single reaction are each labeled with a separate fluorescent label.

In some embodiments, the sequencing comprises pyrosequencing (sequencing by synthesis), comprising: (i) providing a reaction mixture comprising a nucleic acid molecule from a biological sample, a primer complementary to a region of the template nucleic acid molecule, a DNA polymerase, a first enzyme capable of converting pyrophosphate into ATP, and a second enzyme capable using ATP to generates a detectable signal (e.g., a chemiluminescent signal, such as light) in an amount that is proportional to the amount of ATP; (ii) annealing the primer to a single strand of the nucleic acid molecule; (iii) adding one of the four free nucleotides (dNTPs) to allow incorporation of the correct, complementary dNTP onto the template by the DNA polymerase and release of pyrophosphate stoichiometrically; (iv) converting the released pyrophosphate to ATP by the first enzyme; (v) generating a detectable signal by the second enzyme using the ATP; (vi) detecting the generated signal and analyzing the amount of signal generated in a pyrogram; (vii) removing the unincorporated nucleotides; and (viii) repeating steps (iii) to (vii). The method allows sequencing of a single strand of DNA, one base pair at a time, and detecting which base was actually added at each step. The solutions of each type of nucleotides are sequentially added and removed from the reaction. Light is produced only when the nucleotide solution complements the first unpaired base of the template. The order of solutions which produce detectable signals allows the determination of the sequence of the template.

In some embodiments, the method of determining the presence of a TERT fusion (such as, e.g., TRIO:TERT, as disclosed herein) comprises analyzing a nucleic acid sample (e.g., DNA, cDNA, or RNA, or an amplification product thereof) by HPLC. The method may comprise: passing a pressurized liquid solution containing the sample through a column filled with a sorbent, wherein the nucleic acid or protein components in the sample interact differently with the sorbent, causing different flow rates for the different components; separating the components as they flow out the column at different flow rates. In some embodiments, the HPLC is chosen from, e.g., reverse-phase HPLC, size exclusion HPLC, ion-exchange HPLC, and bioaffinity HPLC.

In some embodiments, the method of determining the presence of a TERT fusion (such as, e.g., TRIO:TERT, as disclosed herein) comprises analyzing a nucleic acid sample (e.g., DNA, cDNA, or RNA, or an amplification product thereof) by mass spectrometry. The method may comprise: ionizing the components in the sample (e.g., by chemical or electron ionization); accelerating and subjecting the ionized components to an electric or magnetic field; separating the ionized components based on their mass-to-charge ratios; and detecting the separated components by a detector capable of detecting charged particles (e.g., by an electron multiplier).

II. Methods for Detecting Fusion Proteins

Another aspect of the invention provides a method of detecting the presence of a TERT fusion protein (such as, e.g., TRIO:TERT, as disclosed herein), in a mammal. The method comprises the steps of obtaining a biological sample of a mammal (such as, e.g., from a human cancer), and exposing that sample to at least one reagent that detects a TERT fusion protein (e.g., an antibody that recognizes the TERT fusion but does not recognize the wild type TERT or the wild type fusion partner) to determine whether a TERT fusion protein is present in the biological sample. The detection of a TERT fusion protein indicates the presence of a mutant TERT in the mammal (such as, e.g., in the human cancer). In some embodiments, the TERT fusion protein comprises an amino acid sequence having at least 85%, 90%, 95%, 97%, 98%, or 99% identity with an amino acid sequence of all or part of SEQ ID NO 2 that includes the fusion junction. In some embodiments, the cancer is sarcoma. In some embodiments, the cancer is liposarcoma.

In some embodiments, the reagent that detects a TERT fusion protein can be detectably labeled with, e.g., a radiolabel, a fluorescent label, a bioluminescent label, a chemiluminescent label, an enzyme label, a binding pair label (e.g., biotin/streptavidin), an antigen label, or can include an affinity tag or identifier (e.g., an adaptor, barcode or other sequence identifier). In some embodiments, the labeled reagent can be detected using, e.g., autoradiography, microscopy (e.g., brightfield, fluorescence, or electron microscopy), ELISA, or immunohistochemistry. In some embodiments, the TERT fusion protein can be detected in a biological sample by one or more methods chosen from: such as, e.g., antibody-based detection (western blot, ELISA, immunohistochemistry), size-based detection methods (e.g., HPLC, or mass spectrometry), or protein sequencing.

(1) Antibody-Based Detection

In some embodiments, the method comprises performing a western blot with polypeptides from a biological sample to detect the presence of a TERT fusion protein (such as, e.g., TRIO:TERT, as disclosed herein). In some embodiments, the western blot comprises the steps of: separating the polypeptides by gel electrophoresis; transferring the polypeptides from the gel to a membrane (e.g., a nitrocellulose or polyvinylidene difluoride (PVDF) membrane); blocking the membrane to prevent nonspecific binding by incubating the membrane in a dilute solution of protein (e.g., 3-5% bovine serum albumin (BSA) or non-fat dry milk in Tris-Buffered Saline (TBS) or I-Block, with a minute percentage (e.g., 0.1%) of detergent, such as, e.g., Tween 20 or Triton X-100); exposing the polypeptides to at least one reagent that detects a TERT fusion protein (e.g., an antibody that recognizes the TERT fusion but does not recognize the wild type TERT or the wild type fusion partner); removing unbound or non-specifically bound reagent by washing; and detecting the binding of the reagent with the target protein. In some embodiments, the method comprises two-step detection; exposing the polypeptides to a primary antibody that specifically binds to a TERT fusion protein; removing unbound or non-specifically bound primary antibody by washing; exposing the polypeptides to a secondary antibody that recognizes the primary antibody; removing unbound or non-specifically bound secondary antibody by washing; and detecting the binding of the secondary antibody. In some embodiments, the reagent that detects a TERT fusion protein (e.g., the fusion specific antibody, or the secondary antibody) is directly labeled for detection. In other embodiments, the reagent is linked to an enzyme, and the method further comprises adding a substrate of the enzyme to the membrane; and developing the membrane by detecting a detectable signal produced by the reaction between the enzyme and the substrate. For example, the reagent may be linked with horseradish peroxidase to cleave a chemiluminescent agent as a substrate, producing luminescence in proportion to the amount of the target protein for detection.

In some embodiments, the method comprises performing ELISA with polypeptides from a biological sample to detect the presence of a TERT fusion protein (such as, e.g., TRIO:TERT, as disclosed herein). In some embodiments, the ELISA is chosen from, e.g., direct ELISA, indirect ELISA, sandwich ELISA, and competitive ELISA.

In one embodiment, the direct ELISA comprises the steps of: attaching polypeptides from a biological sample to a surface; blocking the surface to prevent nonspecific binding by incubating the surface in a dilute solution of protein; exposing the polypeptides to an antibody that specifically binds to a TERT fusion protein (e.g., an antibody that recognizes the TERT fusion (such as, e.g., TRIO:TERT, as disclosed herein) but does not recognize the wild type TERT or the wild type fusion partner); removing unbound or non-specifically bound antibody by washing; and detecting the binding of the antibody with the target protein. In some embodiments, the antibody is directly labeled for detection. In other embodiments, the antibody is linked to an enzyme, and the method further comprises adding a substrate of the enzyme; and detecting a detectable signal produced by the reaction between the enzyme and the substrate.

In another embodiment, the indirect ELISA comprises the steps of: attaching polypeptides from a biological sample to a surface; blocking the surface to prevent nonspecific binding by incubating the surface in a dilute solution of protein; exposing the polypeptides to a primary antibody that specifically binds to a TERT fusion protein (such as, e.g., TRIO:TERT, as disclosed herein); removing unbound or non-specifically bound primary antibody by washing; exposing the polypeptides to a secondary antibody that recognizes the primary antibody; removing unbound or non-specifically bound secondary antibody by washing; and detecting the binding of the secondary antibody. In some embodiments, the secondary antibody is directly labeled for detection. In other embodiments, the secondary antibody is linked to an enzyme, and the method further comprises adding a substrate of the enzyme; and detecting a detectable signal produced by the reaction between the enzyme and the substrate.

In some embodiments, the method comprises performing immunohistochemistry with polypeptides from a biological sample to detect the presence of a TERT fusion protein (such as, e.g., TRIO:TERT, as disclosed herein). In some embodiments, the immunohistochemistry comprises the steps of: fixing a cell or a tissue section (e.g., by paraformaldehyde or formalin treatment); permeabilizing the cell or tissue section to allow target accessibility; blocking the cell or tissue section to prevent nonspecific binding; exposing the cell or tissue section to at least one reagent that detects a TERT fusion protein (e.g., an antibody that recognizes the TERT fusion but does not recognize the wild type TERT or the wild type fusion partner); removing unbound or non-specifically bound reagent by washing; and detecting the binding of the reagent with the target protein. In some embodiments, the reagent is directly labeled for detection. In other embodiments, the reagent is linked to an enzyme, and the method further comprises adding a substrate of the enzyme; and detecting a detectable signal produced by the reaction between the enzyme and the substrate. In some embodiments, the immunohistochemistry may comprise the two-step detection as in the indirect ELISA.

(2) Size-Based Detection Methods

In some embodiments, the method of determining the presence of a TERT fusion (such as, e.g., TRIO:TERT, as disclosed herein) comprises analyzing a protein sample by HPLC. The method may comprise: passing a pressurized liquid solution containing the sample through a column filled with a sorbent, wherein the nucleic acid or protein components in the sample interact differently with the sorbent, causing different flow rates for the different components; separating the components as they flow out the column at different flow rates. In some embodiments, the HPLC is chosen from, e.g., reverse-phase HPLC, size exclusion HPLC, ion-exchange HPLC, and bioaffinity HPLC.

In some embodiments, the method of determining the presence of a TERT fusion (such as, e.g., TRIO:TERT, as disclosed herein) comprises analyzing a protein sample by mass spectrometry. The method may comprise: ionizing the components in the sample (e.g., by chemical or electron ionization); accelerating and subjecting the ionized components to an electric or magnetic field; separating the ionized components based on their mass-to-charge ratios; and detecting the separated components by a detector capable of detecting charged particles (e.g., by an electron multiplier).

Detection of a TERT gene fusion or a TERT fusion protein in a patient can lead to assignment of the patient to the newly identified patient population that bears the TERT fusion. Because this patient population can suffer from or be susceptible to a disorder associated with an aberrant TERT expression or activity, or overexpression of TERT, detection of the TERT fusion can also lead to diagnosis of such disorder. Thus, a further aspect of the invention provides a method of stratifying a patient population (e.g., assigning a patient to a group or class) and/or diagnosing a patient, comprising: obtaining a biological sample from the patient, contacting the sample with at least one reagent that detects a TERT gene fusion or a TERT fusion protein to determine whether a TERT fusion is present in the biological sample. The detection of a TERT fusion indicates that the patient belongs to the newly identified patient population that bears the TERT fusion, and/or the presence of a disorder associated with aberrant TERT expression or activity, or overexpression of TERT, such as, e.g., a cancer. The detection of a TERT fusion also identifies a new subtype of cancer, which is characterized by the presence of the TERT fusion. In some embodiments, the cancer is sarcoma. In some embodiments, the cancer is liposarcoma. In certain embodiments, the TERT fusion is TRIO:TERT. In some embodiments, the TRIO:TERT fusion comprises all or part of the nucleotide and/or amino acid sequence (such as, e.g., the fusion junction) set forth in SEQ ID NO: 1 and SEQ ID NO:2, respectively.

Methods for Validating TERT Fusions

TERT gene fusions (such as, e.g., a TRIO:TERT gene fusion) may be evaluated to ensure that the breakpoints are in-frame and can produce a protein product containing the full RT domain, i.e., that the breakpoint occurs such that complete triplet codons are intact, and that the RNA sequence will produce a viable protein. The TERT gene fusion can be transfected into cells to confirm that the protein is functionally active with respect to RT activity and oncogenic activity, cDNA encoding the TERT fusion protein can be produced by standard solid-phase DNA synthesis. Alternatively the TERT fusion cDNA can be produced by RT-PCR using tumor mRNA extracted from samples containing the gene fusion. The DNA amplified can be subcloned into an appropriate vector and characterized by DNA sequence analysis or in vitro/in vivo expression analyses.

Expression vectors containing the TERT gene fusion (such as, e.g., a TRIO:TERT gene fusion) can be introduced into host cells to thereby produce a TERT fusion protein (such as, e.g., a TRIO:TERT fusion protein). The TERT fusion protein expression vector can be a yeast expression vector, a vector for expression in insect cells, e.g., a baculovirus expression vector, or a vector suitable for expression in mammalian cells. Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell.

Cells harboring the expression vector carrying the recombinant TERT gene fusion can then be tested for production of the unique fusion protein via standard western blotting using either an antibody probe that detects the gene product itself or that recognizes a tag peptide (e.g., FLAG tag) that can be added to the gene product via the expression vector (using standard, commercially available reagents). Western blotting can be used to confirm the ectopic expression of the encoded TERT fusion protein by comparing the samples from cells transfected with the vector containing the TERT gene fusion cDNA to cells transfected with the empty expression vector. The functional activity can be assessed by measuring the level of RT activity, e.g., telomere length. Comparison of the level of RT activity between the wild type (normal) form of TERT and the TERT fusion protein can indicate if the TERT fusion protein has elevated activity that could drive oncogenic activity. Whether the TERT gene fusion is oncogenic can be assessed by measuring capacity of the expressed TERT fusion protein to transform cells, that is, to enable cells to grow and proliferate under conditions which are not permissive for growth of normal cells. For example, one method of measuring the transforming activity of the fusion is by assessing if expression of the gene product can allow BaF3 cells to grow in the absence of the growth factor IL3, which is required for the survival and growth of BaF3 cells. Another assay for measuring transforming activity is a soft agar growth assay. This is another standard method which tests the capacity of an introduced gene product to confer the ability to grow in a soft agar matrix, or anchorage-independent conditions. These methods and others can be used to test the oncogenic activity of a TERT gene fusion (such as, e.g., a TRIO:TERT gene fusion) and provide a level of validation of a TERT fusion protein (such as, e.g., a TRIO:TERT fusion protein) as a potential target for treating patients that harbor these fusions.

A change in an activity of a cell can be detected in a cell in culture. e.g., a cell expressing a fusion (e.g., a mammalian cell, a tumor cell or cell line, a recombinant cell). The transfected cell can show a change in response to the expressed fusion, e.g., increased proliferation, changes in morphology, increased tumorigenicity, and/or an acquired transformed phenotype.

All publications and patents mentioned herein are hereby incorporated by reference in their entirety as if each individual publication or patent was specifically and individually indicated to be incorporated by reference. To the extent publications and patents or patent applications incorporated by reference contradict the disclosure contained in the specification, the specification will supersede any contradictory material. Unless otherwise required by context, singular terms shall include the plural and plural terms shall include the singular. The use of "or" means "and/or" unless stated otherwise. The use of the term "including," as well as other forms, such as "includes" and "included," is not limiting. All ranges given in the application encompass the endpoints unless stated otherwise.

Those skilled in the art will recognize, or be able to ascertain using no more than routine experimentation, many equivalents to the specific embodiments of the invention described herein. Such equivalents are intended to be encompassed by the following claims.

I claim:

1. A method for detecting in a patient a TRIO:TERT fusion, said method comprising:
   a) contacting a biological sample from the patient with an oligonucleotide that hybridizes to or amplifies the TRIO:TERT fusion of SEQ ID NO: 1 or a portion thereof comprising a fusion junction; and
   b) detecting (i) binding between the TRIO:TERT fusion and the oligonucleotide or (ii) detecting amplification of the TRIO:TERT fusion.

2. The method of claim 1, wherein the oligonucleotide hybridizes under stringent conditions to (a) a fragment of SEQ ID NO:1 comprising nucleotides 4955-4964 of SEQ ID NO:1, or (b) a complementary oligonucleotide of (a).

3. The method of claim 1, wherein the patient is suffering from or susceptible to a cancer.

4. The method of claim 3, wherein the cancer is sarcoma.

5. The method of claim 3, wherein the cancer is liposarcoma.

* * * * *

SEQUENCE LISTING

```
<160> NUMBER OF SEQ ID NOS: 2

<210> SEQ ID NO 1
<211> LENGTH: 8139
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
atgagcggca gcagcggcgg agccgccgcc cccgccgcgt cctccggccc cgccgcggcg      60
gccagcgcgg ctggctcggg ctgcggggc ggtgccggcg aggggggcaga ggaggcggcc     120 aaggacctgg ccgacatcgc ggccttcttc cgatccgggt ttcgaaaaaa cgatgaaatg     180
aaagctatgg atgttttacc aattttgaag gaaaaagttg cataccttc aggtgggaga      240 gataaacgtg gaggtccat tttaacgttt ccggcccgca gcaatcatga cagaatacga      300
caggaggatc tcaggagact catttcctat ctagcctgta ttcccagcga ggaggtctgc     360
aagcgtggct tcacggtgat cgtggacatg cgtgggtcca agtgggactc catcaagccc     420
cttctgaaga tcctgcagga gtccttcccc tgctgcatcc atgtggccct gatcatcaag     480
ccagacaact tctggcagaa acagaggact aattttggca gttctaaatt tgaatttgag     540
acaaatatgg tctctttaga aggccttacc aaagtagttg atccttctca gctaactcct     600
gagtttgatg gctgcctgga atacaaccac gaagaatgga ttgaaatcag agttgctttt     660
gaagactaca ttagcaatgc cacccacatg ctgtctcggc tggaggaact tcaggacatc     720
ctagctaaga aggagctgcc tcaggattta gagggggctc ggaatatgat cgaggaacat     780
tctcagctga agaagaaggt gattaaggcc cccatcgagg acctggattt ggagggacag     840
aagctgcttc agaggataca gagcagtgaa agctttccca aaaagaactc aggctcaggc     900
```

```
aatgcggacc tgcagaacct cttgcccaag gtgtccacca tgctggaccg gctgcactcg    960
acacggcagc atctgcacca gatgtggcat gtgaggaagc tgaagctgga ccagtgcttc   1020
cagctgaggc tgtttgaaca ggatgctgag aagatgtttg actggatcac acacaacaaa   1080
ggcctgtttc taaacagcta cacagagatt gggaccagcc accctcatgc catggagctt   1140
cagacgcagc acaatcactt tgccatgaac tgtatgaacg tgtatgtaaa tataaaccgc   1200
atcatgtcgg tggccaatcg tctggtggag tctggccact atgcctcgca gcagatcagg   1260
cagatcgcga gtcagctgga gcaggagtgg aaggcgtttg cggcagccct ggatgagcgg   1320
agcaccttgc tggacatgtc ctccattttc caccagaagg ccgaaaagta tatgagcaac   1380
gtggattcat ggtgtaaagc ttgcggtgag gtagaccttc cctcagagct gcaggaccta   1440
gaagatgcca ttcatcacca ccagggaata tatgaacata tcactcttgc ttattctgag   1500
gtcagccaag atgggaagtc gctccttgac aagctccagc ggcccttgac tcccggcagc   1560
tccgattccc tgacagcctc tgccaactac tccaaggccg tgcaccatgt cctggatgtc   1620
atccacgagg tgctgcacca ccagcggcag ctggagaaca tctggcaaca ccgcaaggtc   1680
cggctgcatc agaggctgca gctgtgtgtt ttccagcagg acgttcagca ggtgctagac   1740
tggatcgaga ccacggaga agcatttctg agcaaacata caggtgtggg gaaatctctt   1800
catcgggcca gagcattgca gaaacgtcat gaagattttg aagaagtggc acagaacaca   1860
tacaccaatg cggataaatt actggaagca gcagaacagc tggctcagac tggggaatgt   1920
gaccccgaag agatttatca ggctgcccat cagctggaag accggattca agatttcgtt   1980
cggcgtgttg agcagcgaaa gatcctactg gacatgtcag tgtcctttca cacccatgtg   2040
aaagagctgt ggacgtggct ggaggagctg cagaaggagc tgctggacga cgtgtatgcc   2100
gagtcggtga aggccgtgca ggacctcatc aagcgctttg ccagcagca  gcagaccacc   2160 ctgcaggtga ctgtcaacgt gatcaaggaa ggggaggacc tcatccagca gctcagggac   2220
tctgccatct ccagtaacaa gacccccac aacagctcca tcaaccacat tgagacggtg   2280
ctgcagcagc tggacgaggc agtcgcag atggaggagc tcttccagga gcgcaagatc   2340
aagctggagc tcttcctgca gctgcgcatc ttcgagaggg acgccatcga cattatctca   2400
gacctcgagt cttggaatga tgagcttcct cagcaaatga atgacttcga cacagaagat   2460
ctcacgattg cagagcagcg cctccagcac catgcagaca aagccttgac catgaacaac   2520
ttgacttttg acgtcatcca ccaagggcaa gatcttctgc agtatgtcaa tgaggtccag   2580
gcctctggtg tggagctgct gtgtgataga gatgtagaca tggcaactcg ggtccaggac   2640
ctgctggagt ttcttcatga aaaacagcag gaattggatt tagccgcaga gcagcatcgg   2700
aaacacctgg agcagtgcgt gcagctgcgc cacctgcagg cagaagtgaa acaggtgctg   2760
ggttggatcc gcaacggaga gtccatgtta aatgccggac ttatcacagc cagctcgtta   2820
caagaggcag agcagctcca gcgagagcac gagcagttcc agcatgccat tgagaaaaca   2880
catcagagcg cgctgcaggt gcagcagaag gcagaagcca tgctacaggc caaccactac   2940
gacatggaca tgatccggga ctgcgccgag aaggtggcgt ctcactggca acagctcatg   3000
ctcaagatga agatcgcct caagctcgtc aacgcctctg tcgctttcta caaaacctca   3060
gagcaggtct gcagcgtcct cgagagcctg gaacaggagt acaagagaga agaagactgg   3120
tgtggcgggg cggataagct gggcccaaac tctgagacgg accacgtgac gcccatgatc   3180
agcaagcacc tggagcagaa ggaggcattc ctgaaggctt gcacccttgc tcggaggaat   3240
gcagacgtct tcctgaaata cctgcacagg aacagcgtga acatgccagg aatggtgacg   3300
```

```
cacatcaaag ctcctgaaca gcaagtgaaa aatatcttga atgaactctt ccaacgggag    3360
aacagggtat tgcattactg gaccatgagg aagagacggc tggaccagtg tcagcagtac    3420
gtggtctttg agaggagtgc caagcaggct ttggaatgga tccatgacaa tggcgagttc    3480
tacctttcca cacacacctc cacgggctcc agtatacagc acacccagga gctcctgaaa    3540
gagcacgagg agttccagat aactgcaaag caaaccaaag agagagtgaa gctattgata    3600
cagctggctg atggcttttg tgaaaaaggg catgcccatg cggcagagat aaaaaaatgt    3660
gttactgctg tggataagag gtacagagat ttctctctgc ggatggagaa gtacaggacc    3720
tctttggaaa aagccctggg gatttcttca gattccaaca aatcgagtaa aagtctccag    3780
ctagatatca ttccagccag tatccctggc tcagaggtga acttcgaga tgctgctcat    3840 gaacttaatg aagagaagcg gaaatctgcc cgcaggaaaa agttcataat ggctgagctc    3900
attcaaactg aaaaggctta tgtaagagac ctccgggaat gtatggatac gtacctgtgg    3960
gaaatgacca gtggcgtgga agagattcca cctggcattg taaacaaaga actcatcatc    4020
ttcggaaaca tgcaagaaat ctacgaattt cataataaca tattcctaaa ggagctggaa    4080
aaatatgaac agttgccaga ggatgttgga cattgttttg ttacttgggc agacaagttt    4140
cagatgtatg tcacatattg caaaaataag cctgattcta ctcagctgat attggaacat    4200
gcagggtcct attttgacga gatacagcag cgacatggat tagccaattc catttcttcc    4260
taccttatta aaccagttca gcgaataacg aagtatcagc tccttttaaa agagctgctg    4320
acgtgctgtg aggaaggaaa gggagagatt aaagatggcc tggaggtgat gctcagcgtg    4380
ccgaagcgag ccaatgatgc catgcacctc agcatgctgg aagggtttga tgaaaacatt    4440
gagtctcagg gagaactcat cctacaggaa tccttccaag tgtgggaccc aaaaaacctta    4500 attcgaaagg gtcgagaacg gcatctcttc cttttgaaa tgtccttagt atttagtaaa    4560
gaagtgaaag attccagtgg gagaagcaag tacctttata aaagcaaatt gtttacctca    4620
gagttgggtg tcacagaaca tgttgaagga gacccttgca aatttgcact gtgggtgggg    4680
agaacaccaa cttcagataa taaaaattgtc cttaaggctt ccagcataga gaacaagcag    4740
gactggataa agcatatccg cgaagtcatc caggagcgga cgatccacct gaagggagcc    4800
ctgaaggagc ccattcacat ccctaagacc gctcccgcca caagacagaa gggaaggagg    4860 gatgagagagg atctggacag ccaaggagac ggcagcagcc agcctgatac gatttccatc    4920
gcctcacgga cgtctcagaa cacgctggac agcgataagg tgtcctgcct gaaggagctg    4980
gtggcccgag tgctgcagag gctgtgcgag gcgggcgcga gaacgtgct ggccttcggc    5040 ttcgcgctgc tggacgggc ccgcgggggc cccccgagg ccttcaccac cagcgtgcgc    5100
agctacctgc ccaacacggt gaccgacgca ctgcggggga gggggcgtg ggggctgctg    5160 ctgcgccgcg tgggcgacga cgtgctggtt cacctgctgg cacgctgcgc gctctttgtg    5220
ctggtggctc ccagctgcgc ctaccaggtg tgcgggccgc cgctgtacca gctcggcgct    5280
gccactcagg cccggccccc gccacacgct agtggacccc gaaggcgtct gggatgcgaa    5340
cgggcctgga accatagcgt cagggaggcc ggggtccccc tgggcctgcc agccccgggt    5400
gcgaggaggc gcggggcag tgccagccga agtctgccgt tgcccaagag gcccaggcgt    5460
ggcgctgccc ctgagccgga gcggacgccc gttgggcagg ggtcctgggc ccacccgggc    5520
aggacgcgtg gaccgagtga ccgtggtttc tgtgtggtgt cacctgccag acccgccgaa    5580
gaagccacct cttggagg tgcgctctct ggcacgcgcc actcccaccc atccgtgggc    5640
```

```
cgccagcacc acgcgggccc cccatccaca tcgcggccac cacgtccctg ggacacgcct   5700
tgtcccccgg tgtacgccga gaccaagcac ttcctctact cctcaggcga caaggagcag   5760
ctgcggccct ccttcctact cagctctctg aggcccagcc tgactggcgc tcggaggctc   5820
gtggagacca tctttctggg ttccaggccc tggatgccag ggactcccg caggttgccc    5880 cgcctgcccc agcgctactg gcaaatgcgg cccctgtttc tggagctgct tgggaaccac   5940
gcgcagtgcc cctacggggt gctcctcaag acgcactgcc cgctgcgagc tgcggtcacc   6000
ccagcagccg gtgtctgtgc ccgggagaag ccccagggct ctgtggcggc ccccgaggag   6060
gaggacacag acccccgtcg cctggtgcag ctgctccgcc agcacagcag ccctggcag   6120 gtgtacggct tcgtgcgggc ctgcctgcgc cggctggtgc cccaggcct ctggggctcc    6180 aggcacaacg aacgccgctt cctcaggaac accaagaagt tcatctccct ggggaagcat   6240
gccaagctct cgctgcagga gctgacgtgg aagatgagcg tgcgggactg cgcttggctg   6300
cgcaggagcc caggggttgg ctgtgttccg gccgcagagc accgtctgcg tgaggagatc   6360
ctggccaagt tcctgcactg gctgatgagt gtgtacgtcg tcgagctgct caggtctttc   6420
ttttatgtca cggagaccac gtttcaaaag aacaggctct ttttctaccg gaagagtgtc   6480
tggagcaagt tgcaaagcat tggaatcaga cagcacttga gagggtgca gctgcgggag    6540 ctgtcggaag cagaggtcag gcagcatcgg gaagccaggc ccgccctgct gacgtccaga   6600
ctccgcttca tccccaagcc tgacgggctg cggccgattg tgaacatgga ctacgtcgtg   6660
ggagccagaa cgttccgcag agaaaagagg gccgagcgtc tcacctcgag ggtgaaggca   6720
ctgttcagcg tgctcaacta cgagcgggcg cggcgccccg gcctcctggg cgcctctgtg   6780
ctgggcctgg acgatatcca cagggcctgg cgcaccttcg tgctgcgtgt gcgggcccag   6840
gacccgccgc ctgagctgta ctttgtcaag gtggatgtga cggcgcgta cgacaccatc    6900 ccccaggaca ggctcacgga ggtcatcgcc agcatcatca aaccccagaa cacgtactgc   6960
gtgcgtcggt atgccgtggt ccagaaggcc gcccatgggc acgtccgcaa ggccttcaag   7020
agccacgtct ctaccttgac agacctccag ccgtacatgc gacagttcgt ggctcacctg   7080
caggagacca gcccgctgag ggatgccgtc gtcatcgagc agagctcctc cctgaatgag   7140
gccagcagtg gcctcttcga cgtcttccta cgcttcatgt gccaccacgc cgtgcgcatc   7200
aggggcaagt cctacgtcca gtgccagggg atcccgcagg gctccatcct ctccacgctg   7260
ctctgcagcc tgtgctacgg cgacatggag aacaagctgt ttgcggggat tcggcgggac   7320
gggctgctcc tgcgtttggt ggatgatttc ttgttggtga cacctcacct cacccacgcg   7380
aaaaccttcc tcaggaccct ggtccgaggt gtccctgagt atggctgcgt ggtgaacttg   7440
cggaagacag tggtgaactt ccctgtagaa gacgaggccc tgggtggcac ggcttttgtt   7500
cagatgccgg cccacggcct attccctggt gcggcctgc tgctggatac ccggaccctg    7560
gaggtgcaga gcgactactc cagctatgcc cggacctcca tcagagccag tctcaccttc   7620
aaccgcggct tcaaggctgg gaggaacatg cgtcgcaaac tctttgggt cttgcggctg    7680 aagtgtcaca gcctgttttt ggatttgcag gtgaacagcc tccagacggt gtgcaccaac   7740
atctacaaga tcctcctgct gcaggcgtac aggtttcacg catgtgtgct gcagctccca   7800
tttcatcagc aagtttggaa gaaccccaca tttttcctgc gcgtcatctc tgacacggcc   7860
tccctctgct actccatcct gaaagccaag aacgcaggga tgtcgctggg ggccaagggc   7920
gccgccggcc ctctgccctc cgaggccgtg cagtggctgt gccaccaagc attcctgctc   7980
aagctgactc gacaccgtgt cacctacgtg ccactcctgg ggtcactcag gacagcccag   8040
```

-continued

```
acgcagctga gtcggaagct cccggggacg acgctgactg ccctggaggc cgcagccaac      8100
ccggcactgc cctcagactt caagaccatc ctggactga                             8139
```

<210> SEQ ID NO 2
<211> LENGTH: 2712
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 2

```
Met Ser Gly Ser Ser Gly Gly Ala Ala Ala Pro Ala Ala Ser Ser Gly
1               5                   10                  15

Pro Ala Ala Ala Ser Ala Ala Gly Ser Gly Cys Gly Gly Gly Ala
            20                  25                  30

Gly Glu Gly Ala Glu Glu Ala Ala Lys Asp Leu Ala Asp Ile Ala Ala
        35                  40                  45

Phe Phe Arg Ser Gly Phe Arg Lys Asn Asp Glu Met Lys Ala Met Asp
    50                  55                  60

Val Leu Pro Ile Leu Lys Glu Lys Val Ala Tyr Leu Ser Gly Gly Arg
65                  70                  75                  80

Asp Lys Arg Gly Gly Pro Ile Leu Thr Phe Pro Ala Arg Ser Asn His
                85                  90                  95

Asp Arg Ile Arg Gln Glu Asp Leu Arg Arg Leu Ile Ser Tyr Leu Ala
            100                 105                 110

Cys Ile Pro Ser Glu Glu Val Cys Lys Arg Gly Phe Thr Val Ile Val
        115                 120                 125

Asp Met Arg Gly Ser Lys Trp Asp Ser Ile Lys Pro Leu Leu Lys Ile
    130                 135                 140

Leu Gln Glu Ser Phe Pro Cys Cys Ile His Val Ala Leu Ile Ile Lys
145                 150                 155                 160

Pro Asp Asn Phe Trp Gln Lys Gln Arg Thr Asn Phe Gly Ser Ser Lys
                165                 170                 175

Phe Glu Phe Glu Thr Asn Met Val Ser Leu Glu Gly Leu Thr Lys Val
            180                 185                 190

Val Asp Pro Ser Gln Leu Thr Pro Glu Phe Asp Gly Cys Leu Glu Tyr
        195                 200                 205

Asn His Glu Glu Trp Ile Glu Ile Arg Val Ala Phe Glu Asp Tyr Ile
    210                 215                 220

Ser Asn Ala Thr His Met Leu Ser Arg Leu Glu Glu Leu Gln Asp Ile
225                 230                 235                 240

Leu Ala Lys Lys Glu Leu Pro Gln Asp Leu Glu Gly Ala Arg Asn Met
                245                 250                 255

Ile Glu Glu His Ser Gln Leu Lys Lys Lys Val Ile Lys Ala Pro Ile
            260                 265                 270

Glu Asp Leu Asp Leu Glu Gly Gln Lys Leu Leu Gln Arg Ile Gln Ser
        275                 280                 285

Ser Glu Ser Phe Pro Lys Lys Asn Ser Gly Ser Gly Asn Ala Asp Leu
    290                 295                 300

Gln Asn Leu Leu Pro Lys Val Ser Thr Met Leu Asp Arg Leu His Ser
305                 310                 315                 320

Thr Arg Gln His Leu His Gln Met Trp His Val Arg Lys Leu Lys Leu
                325                 330                 335
```

-continued

```
Asp Gln Cys Phe Gln Leu Arg Leu Phe Glu Gln Asp Ala Glu Lys Met
            340                 345                 350
Phe Asp Trp Ile Thr His Asn Lys Gly Leu Phe Leu Asn Ser Tyr Thr
            355                 360                 365
Glu Ile Gly Thr Ser His Pro His Ala Met Glu Leu Gln Thr Gln His
370                 375                 380
Asn His Phe Ala Met Asn Cys Met Asn Val Tyr Val Asn Ile Asn Arg
385                 390                 395                 400
Ile Met Ser Val Ala Asn Arg Leu Val Glu Ser Gly His Tyr Ala Ser
                405                 410                 415
Gln Gln Ile Arg Gln Ile Ala Ser Gln Leu Glu Gln Glu Trp Lys Ala
            420                 425                 430
Phe Ala Ala Leu Asp Glu Arg Ser Thr Leu Leu Asp Met Ser Ser
            435                 440                 445
Ile Phe His Gln Lys Ala Glu Lys Tyr Met Ser Asn Val Asp Ser Trp
450                 455                 460
Cys Lys Ala Cys Gly Glu Val Asp Leu Pro Ser Glu Leu Gln Asp Leu
465                 470                 475                 480
Glu Asp Ala Ile His His Gln Gly Ile Tyr Glu His Ile Thr Leu
                485                 490                 495
Ala Tyr Ser Glu Val Ser Gln Asp Gly Lys Ser Leu Leu Asp Lys Leu
            500                 505                 510
Gln Arg Pro Leu Thr Pro Gly Ser Ser Asp Ser Leu Thr Ala Ser Ala
            515                 520                 525
Asn Tyr Ser Lys Ala Val His Val Leu Asp Val Ile His Glu Val
530                 535                 540
Leu His His Gln Arg Gln Leu Glu Asn Ile Trp Gln His Arg Lys Val
545                 550                 555                 560
Arg Leu His Gln Arg Leu Gln Leu Cys Val Phe Gln Gln Asp Val Gln
                565                 570                 575
Gln Val Leu Asp Trp Ile Glu Asn His Gly Glu Ala Phe Leu Ser Lys
            580                 585                 590
His Thr Gly Val Gly Lys Ser Leu His Arg Ala Arg Ala Leu Gln Lys
            595                 600                 605
Arg His Glu Asp Phe Glu Glu Val Ala Gln Asn Thr Tyr Thr Asn Ala
610                 615                 620
Asp Lys Leu Leu Glu Ala Ala Glu Gln Leu Ala Gln Thr Gly Glu Cys
625                 630                 635                 640
Asp Pro Glu Glu Ile Tyr Gln Ala Ala His Gln Leu Glu Asp Arg Ile
                645                 650                 655
Gln Asp Phe Val Arg Arg Val Glu Gln Arg Lys Ile Leu Leu Asp Met
            660                 665                 670
Ser Val Ser Phe His Thr His Val Lys Glu Leu Trp Thr Trp Leu Glu
            675                 680                 685
Glu Leu Gln Lys Glu Leu Leu Asp Asp Val Tyr Ala Glu Ser Val Glu
            690                 695                 700
Ala Val Gln Asp Leu Ile Lys Arg Phe Gly Gln Gln Gln Thr Thr
705                 710                 715                 720
Leu Gln Val Thr Val Asn Val Ile Lys Glu Gly Glu Asp Leu Ile Gln
                725                 730                 735
Gln Leu Arg Asp Ser Ala Ile Ser Ser Asn Lys Thr Pro His Asn Ser
            740                 745                 750
```

-continued

```
Ser Ile Asn His Ile Glu Thr Val Leu Gln Gln Leu Asp Glu Ala Gln
            755                 760                 765

Ser Gln Met Glu Glu Leu Phe Gln Glu Arg Lys Ile Lys Leu Glu Leu
    770                 775                 780

Phe Leu Gln Leu Arg Ile Phe Glu Arg Asp Ala Ile Asp Ile Ile Ser
785                 790                 795                 800

Asp Leu Glu Ser Trp Asn Asp Glu Leu Ser Gln Gln Met Asn Asp Phe
                805                 810                 815

Asp Thr Glu Asp Leu Thr Ile Ala Glu Gln Arg Leu Gln His His Ala
            820                 825                 830

Asp Lys Ala Leu Thr Met Asn Asn Leu Thr Phe Asp Val Ile His Gln
        835                 840                 845

Gly Gln Asp Leu Leu Gln Tyr Val Asn Glu Val Gln Ala Ser Gly Val
    850                 855                 860

Glu Leu Leu Cys Asp Arg Asp Val Asp Met Ala Thr Arg Val Gln Asp
865                 870                 875                 880

Leu Leu Glu Phe Leu His Glu Lys Gln Gln Glu Leu Asp Leu Ala Ala
                885                 890                 895

Glu Gln His Arg Lys His Leu Glu Gln Cys Val Gln Leu Arg His Leu
            900                 905                 910

Gln Ala Glu Val Lys Gln Val Leu Gly Trp Ile Arg Asn Gly Glu Ser
        915                 920                 925

Met Leu Asn Ala Gly Leu Ile Thr Ala Ser Ser Leu Gln Glu Ala Glu
    930                 935                 940

Gln Leu Gln Arg Glu His Glu Gln Phe Gln His Ala Ile Glu Lys Thr
945                 950                 955                 960

His Gln Ser Ala Leu Gln Val Gln Gln Lys Ala Glu Ala Met Leu Gln
                965                 970                 975

Ala Asn His Tyr Asp Met Asp Met Ile Arg Asp Cys Ala Glu Lys Val
            980                 985                 990

Ala Ser His Trp Gln Gln Leu Met Leu Lys Met Glu Asp Arg Leu Lys
        995                 1000                1005

Leu Val Asn Ala Ser Val Ala Phe Tyr Lys Thr Ser Glu Gln Val
    1010                1015                1020

Cys Ser Val Leu Glu Ser Leu Glu Gln Glu Tyr Lys Arg Glu Glu
    1025                1030                1035

Asp Trp Cys Gly Gly Ala Asp Lys Leu Gly Pro Asn Ser Glu Thr
    1040                1045                1050

Asp His Val Thr Pro Met Ile Ser Lys His Leu Glu Gln Lys Glu
    1055                1060                1065

Ala Phe Leu Lys Ala Cys Thr Leu Ala Arg Arg Asn Ala Asp Val
    1070                1075                1080

Phe Leu Lys Tyr Leu His Arg Asn Ser Val Asn Met Pro Gly Met
    1085                1090                1095

Val Thr His Ile Lys Ala Pro Glu Gln Gln Val Lys Asn Ile Leu
    1100                1105                1110

Asn Glu Leu Phe Gln Arg Glu Asn Arg Val Leu His Tyr Trp Thr
    1115                1120                1125

Met Arg Lys Arg Arg Leu Asp Gln Cys Gln Gln Tyr Val Val Phe
    1130                1135                1140

Glu Arg Ser Ala Lys Gln Ala Leu Glu Trp Ile His Asp Asn Gly
    1145                1150                1155

Glu Phe Tyr Leu Ser Thr His Thr Ser Thr Gly Ser Ser Ile Gln
```

```
            1160                1165                1170

His Thr Gln Glu Leu Leu Lys Glu His Glu Phe Gln Ile Thr
            1175                1180            1185

Ala Lys Gln Thr Lys Glu Arg Val Lys Leu Leu Ile Gln Leu Ala
    1190                1195                1200

Asp Gly Phe Cys Glu Lys Gly His Ala His Ala Ala Glu Ile Lys
    1205                1210                1215

Lys Cys Val Thr Ala Val Asp Lys Arg Tyr Arg Asp Phe Ser Leu
    1220                1225                1230

Arg Met Glu Lys Tyr Arg Thr Ser Leu Glu Lys Ala Leu Gly Ile
    1235                1240                1245

Ser Ser Asp Ser Asn Lys Ser Ser Lys Ser Leu Gln Leu Asp Ile
    1250                1255                1260

Ile Pro Ala Ser Ile Pro Gly Ser Glu Val Lys Leu Arg Asp Ala
    1265                1270                1275

Ala His Glu Leu Asn Glu Glu Lys Arg Lys Ser Ala Arg Arg Lys
    1280                1285                1290

Glu Phe Ile Met Ala Glu Leu Ile Gln Thr Glu Lys Ala Tyr Val
    1295                1300                1305

Arg Asp Leu Arg Glu Cys Met Asp Thr Tyr Leu Trp Glu Met Thr
    1310                1315                1320

Ser Gly Val Glu Glu Ile Pro Pro Gly Ile Val Asn Lys Glu Leu
    1325                1330                1335

Ile Ile Phe Gly Asn Met Gln Glu Ile Tyr Glu Phe His Asn Asn
    1340                1345                1350

Ile Phe Leu Lys Glu Leu Glu Lys Tyr Glu Gln Leu Pro Glu Asp
    1355                1360                1365

Val Gly His Cys Phe Val Thr Trp Ala Asp Lys Phe Gln Met Tyr
    1370                1375                1380

Val Thr Tyr Cys Lys Asn Lys Pro Asp Ser Thr Gln Leu Ile Leu
    1385                1390                1395

Glu His Ala Gly Ser Tyr Phe Asp Glu Ile Gln Gln Arg His Gly
    1400                1405                1410

Leu Ala Asn Ser Ile Ser Ser Tyr Leu Ile Lys Pro Val Gln Arg
    1415                1420                1425

Ile Thr Lys Tyr Gln Leu Leu Leu Lys Glu Leu Leu Thr Cys Cys
    1430                1435                1440

Glu Glu Gly Lys Gly Glu Ile Lys Asp Gly Leu Glu Val Met Leu
    1445                1450                1455

Ser Val Pro Lys Arg Ala Asn Asp Ala Met His Leu Ser Met Leu
    1460                1465                1470

Glu Gly Phe Asp Glu Asn Ile Glu Ser Gln Gly Glu Leu Ile Leu
    1475                1480                1485

Gln Glu Ser Phe Gln Val Trp Asp Pro Lys Thr Leu Ile Arg Lys
    1490                1495                1500

Gly Arg Glu Arg His Leu Phe Leu Phe Glu Met Ser Leu Val Phe
    1505                1510                1515

Ser Lys Glu Val Lys Asp Ser Ser Gly Arg Ser Lys Tyr Leu Tyr
    1520                1525                1530

Lys Ser Lys Leu Phe Thr Ser Glu Leu Gly Val Thr Glu His Val
    1535                1540                1545

Glu Gly Asp Pro Cys Lys Phe Ala Leu Trp Val Gly Arg Thr Pro
    1550                1555                1560
```

-continued

```
Thr Ser Asp Asn Lys Ile Val Leu Lys Ala Ser Ser Ile Glu Asn
    1565            1570            1575

Lys Gln Asp Trp Ile Lys His Ile Arg Glu Val Ile Gln Glu Arg
    1580            1585            1590

Thr Ile His Leu Lys Gly Ala Leu Lys Glu Pro Ile His Ile Pro
    1595            1600            1605

Lys Thr Ala Pro Ala Thr Arg Gln Lys Gly Arg Arg Asp Gly Glu
    1610            1615            1620

Asp Leu Asp Ser Gln Gly Asp Gly Ser Ser Gln Pro Asp Thr Ile
    1625            1630            1635

Ser Ile Ala Ser Arg Thr Ser Gln Asn Thr Leu Asp Ser Asp Lys
    1640            1645            1650

Val Ser Cys Leu Lys Glu Leu Val Ala Arg Val Leu Gln Arg Leu
    1655            1660            1665

Cys Glu Arg Gly Ala Lys Asn Val Leu Ala Phe Gly Phe Ala Leu
    1670            1675            1680

Leu Asp Gly Ala Arg Gly Gly Pro Pro Glu Ala Phe Thr Thr Ser
    1685            1690            1695

Val Arg Ser Tyr Leu Pro Asn Thr Val Thr Asp Ala Leu Arg Gly
    1700            1705            1710

Ser Gly Ala Trp Gly Leu Leu Leu Arg Arg Val Gly Asp Asp Val
    1715            1720            1725

Leu Val His Leu Leu Ala Arg Cys Ala Leu Phe Val Leu Val Ala
    1730            1735            1740

Pro Ser Cys Ala Tyr Gln Val Cys Gly Pro Pro Leu Tyr Gln Leu
    1745            1750            1755

Gly Ala Ala Thr Gln Ala Arg Pro Pro His Ala Ser Gly Pro
    1760            1765            1770

Arg Arg Arg Leu Gly Cys Glu Arg Ala Trp Asn His Ser Val Arg
    1775            1780            1785

Glu Ala Gly Val Pro Leu Gly Leu Pro Ala Pro Gly Ala Arg Arg
    1790            1795            1800

Arg Gly Gly Ser Ala Ser Arg Ser Leu Pro Leu Pro Lys Arg Pro
    1805            1810            1815

Arg Arg Gly Ala Ala Pro Glu Pro Glu Arg Thr Pro Val Gly Gln
    1820            1825            1830

Gly Ser Trp Ala His Pro Gly Arg Thr Arg Gly Pro Ser Asp Arg
    1835            1840            1845

Gly Phe Cys Val Val Ser Pro Ala Arg Pro Ala Glu Glu Ala Thr
    1850            1855            1860

Ser Leu Glu Gly Ala Leu Ser Gly Thr Arg His Ser His Pro Ser
    1865            1870            1875

Val Gly Arg Gln His His Ala Gly Pro Pro Ser Thr Ser Arg Pro
    1880            1885            1890

Pro Arg Pro Trp Asp Thr Pro Cys Pro Pro Val Tyr Ala Glu Thr
    1895            1900            1905

Lys His Phe Leu Tyr Ser Ser Gly Asp Lys Glu Gln Leu Arg Pro
    1910            1915            1920

Ser Phe Leu Leu Ser Ser Leu Arg Pro Ser Leu Thr Gly Ala Arg
    1925            1930            1935

Arg Leu Val Glu Thr Ile Phe Leu Gly Ser Arg Pro Trp Met Pro
    1940            1945            1950
```

-continued

```
Gly Thr Pro Arg Arg Leu Pro Arg Leu Pro Gln Arg Tyr Trp Gln
    1955                1960                1965

Met Arg Pro Leu Phe Leu Glu Leu Leu Gly Asn His Ala Gln Cys
    1970                1975                1980

Pro Tyr Gly Val Leu Leu Lys Thr His Cys Pro Leu Arg Ala Ala
    1985                1990                1995

Val Thr Pro Ala Ala Gly Val Cys Ala Arg Glu Lys Pro Gln Gly
    2000                2005                2010

Ser Val Ala Ala Pro Glu Glu Asp Thr Asp Pro Arg Arg Leu
    2015                2020                2025

Val Gln Leu Leu Arg Gln His Ser Ser Pro Trp Gln Val Tyr Gly
    2030                2035                2040

Phe Val Arg Ala Cys Leu Arg Leu Val Pro Pro Gly Leu Trp
    2045                2050                2055

Gly Ser Arg His Asn Glu Arg Arg Phe Leu Arg Asn Thr Lys Lys
    2060                2065                2070

Phe Ile Ser Leu Gly Lys His Ala Lys Leu Ser Leu Gln Glu Leu
    2075                2080                2085

Thr Trp Lys Met Ser Val Arg Asp Cys Ala Trp Leu Arg Arg Ser
    2090                2095                2100

Pro Gly Val Gly Cys Val Pro Ala Ala Glu His Arg Leu Arg Glu
    2105                2110                2115

Glu Ile Leu Ala Lys Phe Leu His Trp Leu Met Ser Val Tyr Val
    2120                2125                2130

Val Glu Leu Leu Arg Ser Phe Phe Tyr Val Thr Glu Thr Thr Phe
    2135                2140                2145

Gln Lys Asn Arg Leu Phe Phe Tyr Arg Lys Ser Val Trp Ser Lys
    2150                2155                2160

Leu Gln Ser Ile Gly Ile Arg Gln His Leu Lys Arg Val Gln Leu
    2165                2170                2175

Arg Glu Leu Ser Glu Ala Glu Val Arg Gln His Arg Glu Ala Arg
    2180                2185                2190

Pro Ala Leu Leu Thr Ser Arg Leu Arg Phe Ile Pro Lys Pro Asp
    2195                2200                2205

Gly Leu Arg Pro Ile Val Asn Met Asp Tyr Val Val Gly Ala Arg
    2210                2215                2220

Thr Phe Arg Arg Glu Lys Arg Ala Glu Arg Leu Thr Ser Arg Val
    2225                2230                2235

Lys Ala Leu Phe Ser Val Leu Asn Tyr Glu Arg Ala Arg Arg Pro
    2240                2245                2250

Gly Leu Leu Gly Ala Ser Val Leu Gly Leu Asp Asp Ile His Arg
    2255                2260                2265

Ala Trp Arg Thr Phe Val Leu Arg Val Arg Ala Gln Asp Pro Pro
    2270                2275                2280

Pro Glu Leu Tyr Phe Val Lys Val Asp Val Thr Gly Ala Tyr Asp
    2285                2290                2295

Thr Ile Pro Gln Asp Arg Leu Thr Glu Val Ile Ala Ser Ile Ile
    2300                2305                2310

Lys Pro Gln Asn Thr Tyr Cys Val Arg Arg Tyr Ala Val Val Gln
    2315                2320                2325

Lys Ala Ala His Gly His Val Arg Lys Ala Phe Lys Ser His Val
    2330                2335                2340

Ser Thr Leu Thr Asp Leu Gln Pro Tyr Met Arg Gln Phe Val Ala
```

-continued

```
                2345                2350                2355

His Leu Gln Glu Thr Ser Pro Leu Arg Asp Ala Val Val Ile Glu
            2360                2365                2370

Gln Ser Ser Ser Leu Asn Glu Ala Ser Ser Gly Leu Phe Asp Val
        2375                2380                2385

Phe Leu Arg Phe Met Cys His His Ala Val Arg Ile Arg Gly Lys
    2390                2395                2400

Ser Tyr Val Gln Cys Gln Gly Ile Pro Gln Gly Ser Ile Leu Ser
2405                2410                2415

Thr Leu Leu Cys Ser Leu Cys Tyr Gly Asp Met Glu Asn Lys Leu
    2420                2425                2430

Phe Ala Gly Ile Arg Arg Asp Gly Leu Leu Leu Arg Leu Val Asp
        2435                2440                2445

Asp Phe Leu Leu Val Thr Pro His Leu Thr His Ala Lys Thr Phe
            2450                2455                2460

Leu Arg Thr Leu Val Arg Gly Val Pro Glu Tyr Gly Cys Val Val
                2465                2470                2475

Asn Leu Arg Lys Thr Val Val Asn Phe Pro Val Glu Asp Glu Ala
                    2480                2485                2490

Leu Gly Gly Thr Ala Phe Val Gln Met Pro Ala His Gly Leu Phe
                        2495                2500                2505

Pro Trp Cys Gly Leu Leu Leu Asp Thr Arg Thr Leu Glu Val Gln
                            2510                2515                2520

Ser Asp Tyr Ser Ser Tyr Ala Arg Thr Ser Ile Arg Ala Ser Leu
                2525                2530                2535

Thr Phe Asn Arg Gly Phe Lys Ala Gly Arg Asn Met Arg Arg Lys
                    2540                2545                2550

Leu Phe Gly Val Leu Arg Leu Lys Cys His Ser Leu Phe Leu Asp
                        2555                2560                2565

Leu Gln Val Asn Ser Leu Gln Thr Val Cys Thr Asn Ile Tyr Lys
                            2570                2575                2580

Ile Leu Leu Leu Gln Ala Tyr Arg Phe His Ala Cys Val Leu Gln
                    2585                2590                2595

Leu Pro Phe His Gln Gln Val Trp Lys Asn Pro Thr Phe Phe Leu
                        2600                2605                2610

Arg Val Ile Ser Asp Thr Ala Ser Leu Cys Tyr Ser Ile Leu Lys
                            2615                2620                2625

Ala Lys Asn Ala Gly Met Ser Leu Gly Ala Lys Gly Ala Ala Gly
                                2630                2635                2640

Pro Leu Pro Ser Glu Ala Val Gln Trp Leu Cys His Gln Ala Phe
                                    2645                2650                2655

Leu Leu Lys Leu Thr Arg His Arg Val Thr Tyr Val Pro Leu Leu
                                        2660                2665                2670

Gly Ser Leu Arg Thr Ala Gln Thr Gln Leu Ser Arg Lys Leu Pro
                            2675                2680                2685

Gly Thr Thr Leu Thr Ala Leu Glu Ala Ala Ala Asn Pro Ala Leu
                                2690                2695                2700

Pro Ser Asp Phe Lys Thr Ile Leu Asp
                                    2705                2710
```